(12) United States Patent
Yamazaki et al.

(10) Patent No.: US 12,196,967 B2
(45) Date of Patent: Jan. 14, 2025

(54) COMPOSITE DEVICE

(71) Applicant: Semiconductor Energy Laboratory Co., Ltd., Kanagawa-ken (JP)

(72) Inventors: Shunpei Yamazaki, Tokyo (JP); Takayuki Ikeda, Kanagawa (JP); Shuichi Katsui, Kanagawa (JP); Yoshiaki Oikawa, Kanagawa (JP); Kensuke Yoshizumi, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 81 days.

(21) Appl. No.: 17/615,252

(22) PCT Filed: May 22, 2020

(86) PCT No.: PCT/IB2020/054868
§ 371 (c)(1),
(2) Date: Nov. 30, 2021

(87) PCT Pub. No.: WO2020/245694
PCT Pub. Date: Dec. 10, 2020

(65) Prior Publication Data
US 2022/0236569 A1 Jul. 28, 2022

(30) Foreign Application Priority Data
Jun. 7, 2019 (JP) ................ 2019-107172

(51) Int. Cl.
*G02B 27/01* (2006.01)
*A61B 5/00* (2006.01)
*G06F 3/01* (2006.01)

(52) U.S. Cl.
CPC ........ *G02B 27/0172* (2013.01); *A61B 5/6803* (2013.01); *A61B 5/742* (2013.01); *G06F 3/014* (2013.01); *G02B 2027/014* (2013.01)

(58) Field of Classification Search
CPC .......... G02B 27/0172; G02B 2027/014; A61B 5/6803; A61B 5/742; G06F 3/014
See application file for complete search history.

(56) References Cited

U.S. PATENT DOCUMENTS 8,922,366 B1 12/2014 Honore et al.
9,128,305 B2 * 9/2015 Honore ................ A61B 3/0041
(Continued)

FOREIGN PATENT DOCUMENTS

CN 101204323 A 6/2008
CN 102834051 A 12/2012
(Continued)

OTHER PUBLICATIONS

International Search Report (Application No. PCT/IB2020/054868) Dated Aug. 11, 2020.
(Continued)

*Primary Examiner* — Towfiq Elahi
(74) *Attorney, Agent, or Firm* — Husch Blackwell LLP

(57) ABSTRACT

An electronic device with reduced power consumption is provided. A multifunction electronic device that is easily reduced in weight or size is provided. A composite device includes a sensor device and a display device. The sensor device includes a first communication portion and a sensor portion and can be worn on a human body. The display device includes a display portion, a second communication portion, and a control portion. The first communication portion has a function of transmitting a signal including information obtained by the sensor portion. The second communication portion has a function of receiving the signal. The control portion has a function of returning from a resting state in accordance with the signal. The control portion has a function of generating first image data on the basis of the information and outputting the first image data
(Continued)

to the display portion. The display portion has a function of displaying an image on the basis of the first image data.

14 Claims, 14 Drawing Sheets

(56) References Cited

U.S. PATENT DOCUMENTS

| | | | |
|---|---|---|---|
| 9,557,582 | B2 | 1/2017 | Honore et al. |
| 2001/0020922 | A1 | 9/2001 | Yamazaki et al. |
| 2002/0021274 | A1 | 2/2002 | Koyama et al. |
| 2002/0113546 | A1 | 8/2002 | Seo et al. |
| 2005/0134528 | A1* | 6/2005 | Valliath ............... G02F 1/1347 345/32 |
| 2006/0250259 | A1 | 11/2006 | Izumi |
| 2007/0285225 | A1 | 12/2007 | Koyama et al. |
| 2008/0079565 | A1 | 4/2008 | Koyama |
| 2008/0146947 | A1 | 6/2008 | Kojima et al. |
| 2008/0294033 | A1 | 11/2008 | Yamazaki |
| 2012/0323101 | A1 | 12/2012 | Kohno et al. |
| 2013/0297874 | A1 | 11/2013 | Kurokawa |
| 2013/0297889 | A1 | 11/2013 | Fujita |
| 2013/0326157 | A1 | 12/2013 | Hara |
| 2015/0091711 | A1* | 4/2015 | Kosonen ............... H04M 3/02 340/407.1 |
| 2016/0233469 | A1 | 8/2016 | Kimura |
| 2016/0255944 | A1* | 9/2016 | Baranski ............ A44C 5/2071 |
| 2016/0320622 | A1* | 11/2016 | Yoshida ............... G06F 1/163 |
| 2017/0086743 | A1* | 3/2017 | Bushnell ............ A61B 5/681 |
| 2017/0097524 | A1 | 4/2017 | Honore et al. |
| 2017/0160801 | A1 | 6/2017 | Miyaguchi |
| 2017/0205874 | A1 | 7/2017 | Miyaguchi |
| 2017/0300261 | A1 | 10/2017 | Kurokawa |
| 2018/0052508 | A1 | 2/2018 | Okamoto et al. |
| 2019/0290197 | A1* | 9/2019 | Nothacker ......... A61B 10/0064 |
| 2020/0127064 | A1 | 4/2020 | Ikeda. et al. |
| 2020/0196951 | A1* | 6/2020 | Latva-Käyrä .......... G16H 40/63 |
| 2021/0111196 | A1 | 4/2021 | Yamazaki et al. |
| 2021/0143209 | A1 | 5/2021 | Yamazaki et al. |
| 2021/0159222 | A1 | 5/2021 | Yamazaki et al. |
| 2021/0327865 | A1 | 10/2021 | Yamazaki et al. |
| 2021/0384355 | A1 | 12/2021 | Sato et al. |

FOREIGN PATENT DOCUMENTS

| | | |
|---|---|---|
| CN | 105359167 A | 2/2016 |
| EP | 1 932 466 A2 | 6/2008 |
| EP | 2 554 116 A1 | 2/2013 |
| JP | 56-023503 | 3/1981 |
| JP | 2002-324673 A | 11/2002 |
| JP | 2008-099834 A | 5/2008 |
| JP | 2008-148766 A | 7/2008 |
| JP | 2011-212117 A | 10/2011 |
| JP | 2016-144563 A | 8/2016 |
| JP | 2016-534767 | 11/2016 |
| JP | 2017-192492 A | 10/2017 |
| WO | WO 2011/121897 A1 | 10/2011 |
| WO | WO 2014/209657 A1 | 12/2014 |
| WO | WO 2020/261028 A1 | 12/2020 |

OTHER PUBLICATIONS

Written Opinion (Application No. PCT/IB2020/054868) Dated Aug. 11, 2020.

* cited by examiner

COMPOSITE DEVICE

This application is a 371 of international application PCT/IB2020/054868 filed on May 22, 2020 which is incorporated herein by reference.

TECHNICAL FIELD

One embodiment of the present invention relates to a display device. One embodiment of the present invention relates to a sensor device. One embodiment of the present invention relates to an image capturing device.

Note that one embodiment of the present invention is not limited to the above technical field. Examples of the technical field of one embodiment of the present invention disclosed in this specification and the like include a semiconductor device, a display device, a light-emitting device, a power storage device, a memory device, an electronic device, a lighting device, an input device, an input/output device, a driving method thereof, and a manufacturing method thereof. A semiconductor device generally means a device that can function by utilizing semiconductor characteristics.

BACKGROUND ART

A device for virtual reality (VR) or augmented reality (AR) has been actively developed in recent years.

Examples of a display device that can be used for a display panel include, typically, a liquid crystal display device, a light-emitting device including a light-emitting element such as an organic EL (Electro Luminescence) element or a light-emitting diode (LED), and electronic paper performing display by an electrophoretic method or the like.

For example, the basic structure of an organic EL element is a structure in which a layer containing a light-emitting organic compound is provided between a pair of electrodes. By applying a voltage to this element, light emission can be obtained from the light-emitting organic compound. A display device using such an organic EL element does not need a backlight that is necessary for a liquid crystal display device and the like; thus, a thin, lightweight, high-contrast, and low-power display device can be achieved. Patent Document 1, for example, discloses an example of a display device using an organic EL element.

REFERENCE

Patent Document

[Patent Document 1] Japanese Published Patent Application No. 2002-324673

SUMMARY OF THE INVENTION

Problems to be Solved by the Invention

Since a device for VR or AR is worn on a human body, a small and lightweight device is preferable for the VR or AR device. However, when the device is used for a long time in an environment with no power supply, a battery having large capacitance needs to be mounted, which makes it difficult to reduce the size or weight of the device. In addition, an increase in power consumption caused by an increase in functions of the device requires a battery having larger capacitance.

In recent years, because of a rise in health awareness, a device with which a health condition is grasped and monitored in daily life has been required. For example, medical devices targeted at individuals, such as a hemadynamometer and an electrocardiograph, have been reduced in size and price. Furthermore, functions of information terminals such as a smartphone and a tablet have been increased by addition of a function of managing obtained data, or the like. In contrast, people who are not very conscious of health feel that such daily measurement is troublesome in many cases; thus, polarization between people who take care of their health and people who do not do it tends to occur.

One object of one embodiment of the present invention is to provide an electronic device having reduced power consumption. Another object is to provide a multifunction electronic device that facilitates a reduction in weight or size. Another object is to provide an electronic device that facilitates management of health condition. Another object is to provide an electronic device in which an image having enhanced reality can be displayed. Another object is to provide a novel display device, a novel sensor device, a novel electronic device, a novel composite device, or the like.

Note that the description of these objects does not preclude the existence of other objects. One embodiment of the present invention does not have to achieve all these objects. Objects other than these can be derived from the description of the specification, the drawings, the claims, and the like.

Means for Solving the Problems

One embodiment of the present invention is a composite device including a sensor device and a display device. The sensor device includes a first communication portion and a sensor portion and can be worn on a human body. The display device includes a display portion, a second communication portion, and a control portion. The first communication portion has a function of transmitting a signal including information obtained by the sensor portion. The second communication portion has a function of receiving the signal. The control portion has a function of returning from a resting state in accordance with the signal. The control portion has a function of generating first image data on the basis of the information and outputting the first image data to the display portion. The display portion has a function of displaying an image on the basis of the first image data.

In the above, the sensor device is preferably configured to be able to be worn on an eyeball. In the above, the sensor device is preferably configured to be able to be attached to (worn on) skin. Alternatively, the sensor device is preferably configured to be able to be worn on a wrist, a finger, or an arm. Alternatively, the sensor device is preferably fixed to clothes.

In the above, the sensor portion preferably has a function of detecting one or more of a blood sugar level, a heart rate, a blood pressure, a body temperature, a degree of oxygen saturation, and a neutral fat concentration.

In the above, in the display portion, the pixel density is preferably higher than or equal to 1000 ppi and less than or equal to 10000 ppi, and the number of pixels in a scan line direction or a signal line direction is preferably greater than or equal to 2000 and less than or equal to 10000.

In the above, the display device preferably includes an image capturing portion. In that case, the control portion preferably has a function of generating the first image data on the basis of the information included in the signal and second image data input from the image capturing portion and outputting the first image data to the display portion.

Effect of the Invention

According to one embodiment of the present invention, an electronic device having reduced power consumption can be provided. Alternatively, a multifunction electronic device that facilitates a reduction in weight or size can be provided. Alternatively, an electronic device that facilitates management of health condition can be provided. Alternatively, an electronic device in which an image having enhanced reality can be displayed can be provided. Alternatively, a novel display device, a novel sensor device, a novel electronic device, a novel composite device, or the like can be provided.

Note that the description of these effects does not preclude the existence of other effects. One embodiment of the present invention does not have to have all of these effects. Effects other than these can be derived from the description of the specification, the drawings, the claims, and the like.

MODE FOR CARRYING OUT THE INVENTION

Figure 1A:
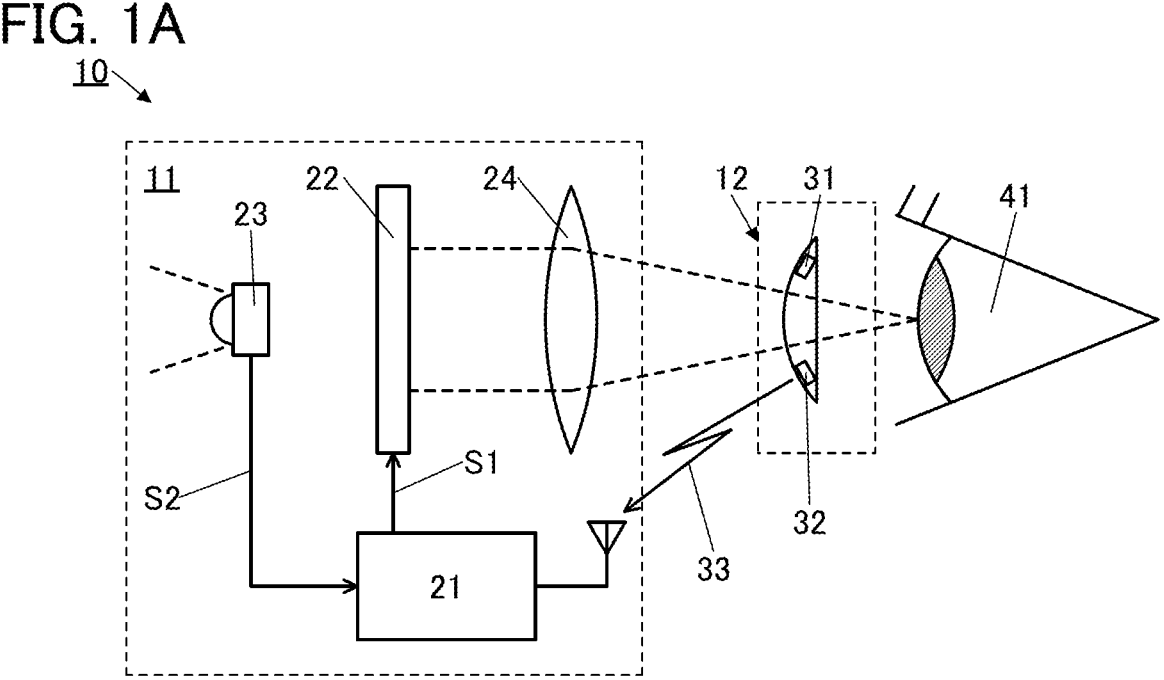
FIG. 1A and FIG. 1B are diagrams illustrating a structure example of a composite device.

Hereinafter, embodiments are described with reference to the drawings. Note that the embodiments can be implemented in many different modes, and it is readily understood by those skilled ion the art that modes and details thereof can be changed in various ways without departing from the spirit and scope thereof. Thus, the present invention should not be construed as being limited to the following description of the embodiments.

Note that in structures of the invention described below, the same portions or portions having similar functions are denoted by the same reference numerals in different drawings, and a description thereof is not repeated. Furthermore, the same hatch pattern is used for the portions having similar functions, and the portions are not especially denoted by reference numerals in some cases.

Note that in each drawing described in this specification, the size, the layer thickness, or the region of each component is exaggerated for clarity in some cases. Therefore, they are not limited to the illustrated scale.

Note that in this specification and the like, the ordinal numbers such as "first" and "second" are used in order to avoid confusion among components and do not limit the number.

Embodiment 1

In this embodiment, a display device and a sensor device of one embodiment of the present invention and a composite device including them are described with reference to drawings.

[Structure Example of Composite Device]

FIG. 1A illustrates a schematic diagram of a composite device 10. The composite device 10 includes a display device 11 and a sensor device 12.

The display device 11 includes a control portion 21, a display portion 22, an image capturing portion 23, and a lens 24. The sensor device 12 includes a sensor portion 31 and a communication portion 32.

The display device 11 preferably has a structure that can be worn on a head of a human body. For example, the display device 11 can be used as a glasses-type display device or a goggle-type display device. Furthermore, a structure in which an image is recognized by one eye may be employed.

The sensor device 12 preferably has a structure that can be worn on a human body. FIG. 1A illustrates an example in which the sensor device 12 can be worn on an eyeball of a human body. The sensor device 12 illustrated in FIG. 1A can also be used as a contact lens. Note that the structure of the sensor device 12 is not limited to this and can have various modes.

The display portion 22 included in the display device 11 includes a plurality of pixels and has a function of displaying images. The pixel includes one or more of display elements. A variety of display elements such as a light-emitting element, a liquid crystal element, a microcapsule, an electrophoretic element, an electrowetting element, an electrofluidic element, an electrochromic element, and a MEMS element can be used as the display element.

In particular, the use of a light-emitting element as the display element included in the display portion 22 can obtain high contrast, and thus an image with a strong sense of reality can be displayed. As the light-emitting element, an organic EL element, an LED element, an inorganic EL element, or the like can be used. In particular, an organic EL element is preferably used.

Examples of the LED element include a macro LED (also referred to as a huge LED), a mini LED, a micro LED, and the like in descending order in size. Here, an LED chip whose one side size is larger than 1 mm is called a macro LED, an LED chip whose one side size is larger than 100 μm and smaller than or equal to 1 mm is called a mini LED, and an LED chip whose one side size is smaller than or equal to 100 μm is called a micro LED. It is particularly preferable to use a micro LED as an LED element applied to the pixel. The use of a micro LED can achieve an extremely high-resolution display device.

The display portion 22 preferably has higher resolution. The pixel density of the display portion 22 can be higher than or equal to 1000 ppi and less than or equal to 50000 ppi, preferably higher than or equal to 2000 ppi and less than or equal to 20000 ppi, further preferably higher than or equal to 3000 ppi and less than or equal to 10000 ppi, still further preferably higher than or equal to 5000 ppi and less than or equal to 10000 ppi. Typically, the pixel density can be higher than or equal to 4500 ppi and less than or equal to 5500 ppi, higher than or equal to 5500 ppi and less than or equal to 6500 ppi, or higher than or equal to 6500 ppi and less than or equal to 7500 ppi.

Moreover, the display portion 22 preferably has higher definition. The number of pixels in the display portion 22 in the scan line direction or the signal line direction is, for example, greater than or equal to 1000 and less than or equal to 20000, preferably greater than or equal to 2000 and less than or equal to 10000, further preferably greater than or equal to 3000 and less than or equal to 10000. When two display portions 22 are provided for a left eye and a right eye, the shape of the display region can be close to a regular square (the ratio of the lateral length to the longitudinal length is greater than or equal to 0.8 and less than or equal to 1.2). In contrast, when one display region is used for a right eye and a left eye, the shape of the display region is preferably a laterally-long rectangle (e.g., the ratio of the lateral length to the longitudinal length is greater than or equal to 1.5 and less than or equal to 5.0). Furthermore, the display portion 22 may meet the standard of television whose aspect ratio is 16:9, and in that case, the display portion 22 can have the definition of the FHD standard, the 4K2K standard, or the 8K4K standard.

Moreover, as the display portion 22, what is called a see-through panel, which transmits external light, may be used. Accordingly, the display device 11 can be used as a device for AR. In that case, the display device 11 may have a structure without the image capturing portion 23.

The image capturing portion 23 is provided in a position at which an image of what lies in front of the image capturing portion 23 can be taken when the display device 11 is worn. The image taken by the image capturing portion 23 can be displayed on the display portion 22 through the control portion 21.

As the image capturing portion 23, a camera can be favorably used. An image capturing element included in the image capturing portion 23 preferably has higher definition. In particular, the image capturing element preferably includes pixels whose number is the same as or greater than the number of pixels included in the display portion 22.

The control portion 21 has a function of generating an image signal S1 and outputting the image signal S1 to the display portion 22. The control portion 21 has a function of controlling the operation of the image capturing portion 23 and obtaining an image signal S2 input from the image capturing portion 23. The control portion 21 has a function of receiving a signal 33 supplied from the sensor device 12 and generating the image signal S1 output to the display portion 22 on the basis of information included in the signal 33.

For example, the control portion 21 can display an image taken by the image capturing portion 23 on the display portion 22 with almost no delay on the basis of image data that is included in the image signal S2 and taken by the image capturing portion 23. Furthermore, the control portion 21 can synthesize an image formed on the basis of information obtained by the sensor device 12 and an image included in the image signal S2 and can display the synthe-sized image on the display portion 22. Accordingly, what is called AR display or MR (Mixed Reality) display can be performed.

The sensor device 12 includes the sensor portion 31 and the communication portion 32. The sensor device 12 can transmit information obtained by the sensor portion 31 to the control portion 21 in the display device 11 through the communication portion 32.

The sensor portion 31 can include a sensor that can obtain various kinds of biological information. For example, for the sensor portion, a contact-type sensor that is in contact with a human body, an optical sensor using light, an electric sensor that uses an electron signal from a human body, a sensor that can obtain a constituent or a property of body fluids (e.g., a lachrymal fluid or sweat), or the like can be used.

For example, the sensor device 12 illustrated in FIG. 1A can measure the concentration of salinity, glucose, or the like from a lachrymal fluid by the sensor portion 31. For example, from the concentration of glucose measured by the sensor portion 31, a user's blood sugar level can be estimated.

The communication portion 32 has a function of transmitting the signal 33 including information obtained by the sensor portion 31 to the display device 11. The communication portion 32 can have a structure including an antenna, a signal generation circuit, a modulation circuit, or the like.

FIG. 1A illustrates an eyeball 41 of a user. Here, for easy understanding, a space is illustrated between the eyeball 41 and the sensor device 12; however, the sensor device 12 can be worn to be in contact with the eyeball 41, in practice.

The lens 24 is provided between the display portion 22 and the sensor device 12 and has a function of focus adjustment. Note that a structure in which the lens 24 is not provided may be employed in the case where focus adjustment is not necessary because a sufficient distance is provided between the display portion 22 and the eyeball 41 or the case where the sensor device 12 has a function of focus adjustment, for example.

The user can see an image displayed on the display portion 22 through the sensor device 12 and the lens 24.

When the user wears the display device 11 on his/her head and wears the sensor device 12 on the eyeball 41, the communication distance between a communication portion 25 and the communication portion 32 becomes extremely small. Thus, power needed for communication can be extremely low, so that the power consumption of the composite device 10 can be reduced. Furthermore, since power needed for communication is low, the influence of communication radio waves on health can be small enough to be ignored.

Figure 1B:
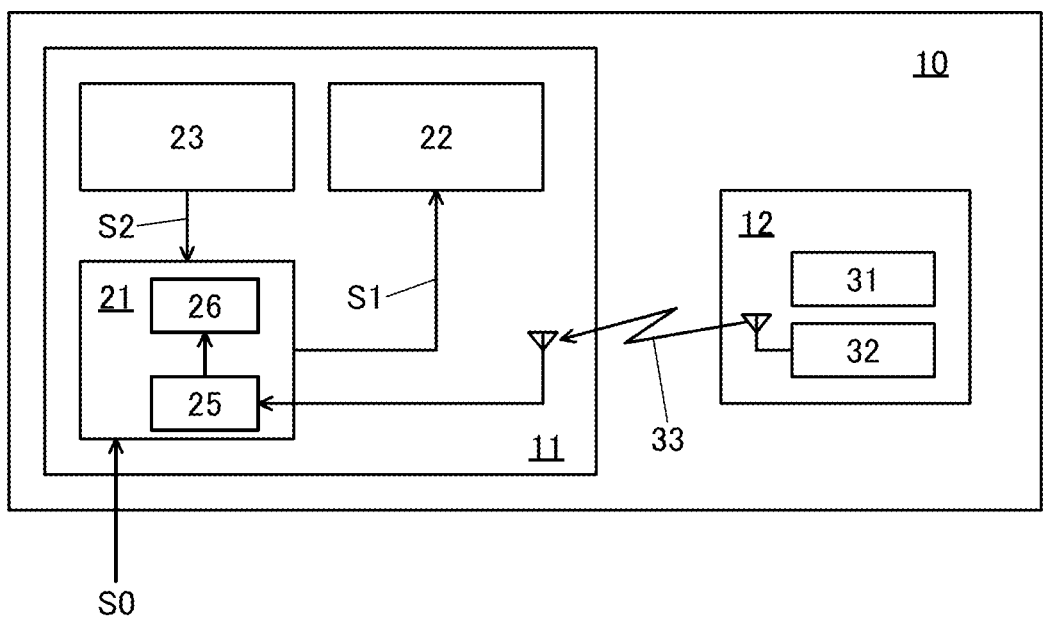

FIG. 1B is a block diagram of the composite device 10.

The control portion 21 includes the communication portion 25 and an image generation portion 26. To the control portion 21, the image signal S2 is input from the image capturing portion 23 and the signal 33 is input from the sensor device 12. Furthermore, an image signal S0 may be input from the outside. Moreover, the image signal S1 is output from the control portion 21 to the display portion 22.

The communication portion 25 has a function of receiving the signal 33 transmitted from the sensor device 12 and outputting data included in the signal to the image generation portion 26. The communication portion 25 can have a structure including an antenna, a demodulation circuit, or the like, for example.

Note that in the case where the communication portion 25 and the communication portion 32 have a structure that enables mutual communication, each of them may include a demodulation circuit and a modulation circuit.

The communication portion 25 preferably has a function of switching to a state where operation is stopped (also referred to as a resting state) in a period during which the signal 33 is not input. In that case, the control portion 21 has a function of returning the communication portion 25 from the resting state on the basis of the input of the signal 33. Bringing the communication portion 25 including an analog circuit into the resting state in a period during which operation is not necessary can reduce the power consumption of the control portion 21 considerably. Furthermore, the display device 11 can be reduced in size and weight.

Figure 2:
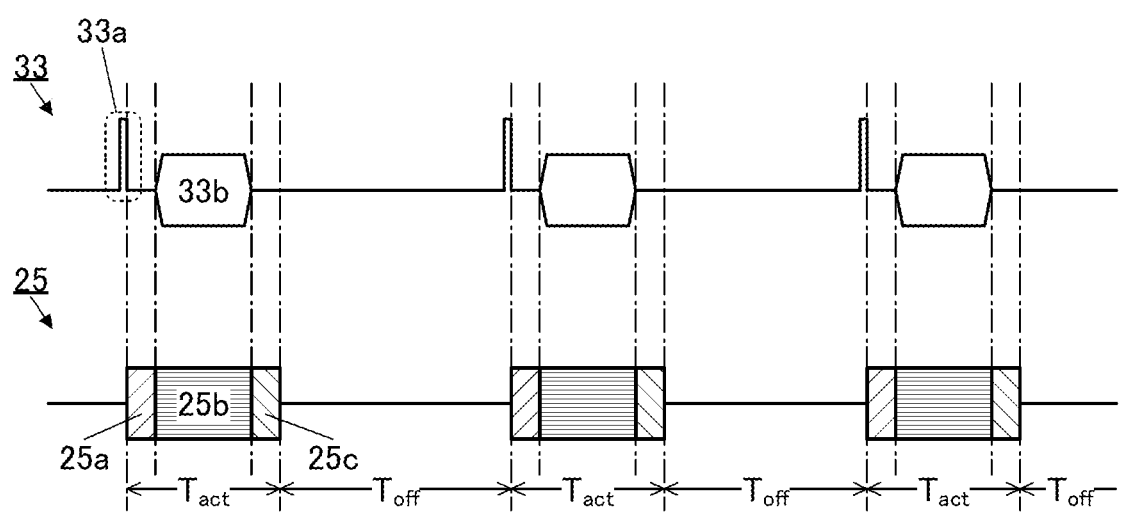
FIG. 2 is a diagram illustrating an operation example of a display device.

FIG. 2 is a schematic timing chart showing the operation of the signal 33 and the communication portion 25. One signal of the signal 33 has a pulse signal 33a and a signal 33b including data. As shown in FIG. 2, as the signal 33 transmitted from the communication portion 32, a set of the pulse signal 33a and the signal 33b is output intermittently.

The operation of the communication portion 25 is roughly divided into three: a returning operation 25a, a processing operation 25b, and a resting operation 25c, and the three forms one set. When the control portion 21 receives the pulse signal 33a, the control portion 21 controls the communication portion 25 to execute the returning operation 25a. The communication portion 25 is made to return from the resting state by the returning operation 25a. After the returning operation 25a, the communication portion 25 demodulates the received signal 33b, generates data, and outputs the data to the image generation portion 26 in the processing operation 25b. After the output, the resting operation 25c is performed, and then the communication portion 25 is brought into the resting state.

Here, in FIG. 2, an operation period $T_{act}$ and a resting period $T_{off}$ are shown. As the resting period $T_{off}$ with respect to the operation period $T_{act}$ is longer, the power consumption can be reduced. For example, sampling frequencies needed for monitoring a change of biological information of a human can be less than or equal to 10 Hz, less than or equal to 5 Hz, less than or equal to 1 Hz, or less than or equal to 0.1 Hz, and thus the receiving frequencies of the signal 33 can be substantially equal to the sampling frequencies. Furthermore, the operation period $T_{act}$ can be an extremely short time (e.g., several ten microseconds to several ten milliseconds), and thus the communication portion 25 can be in the resting state in most of the period.

When data included in the signal 33 is input from the communication portion 25, the image generation portion 26 illustrated in FIG. 1B has a function of generating image data on the basis of the input data and synthesizing an image data formed on the basis of the image data and image data included in the image signal S2 input from the image capturing portion 23. The control portion 21 generates the image signal S1 including the synthesized image data and outputs the image signal S1 to the display portion 22.

Furthermore, in the case where the image signal S0 is input from the outside, the image generation portion 26 may have a function of synthesizing an image data formed on the basis of image data included in the image signal S0 and image data generated on the basis of the data included in the signal 33

Moreover, the image generation portion 26 may have a function of synthesizing an image data formed on the basis of image data included in the image signal S1, the image data included in the image signal S0, and the image data generated on the basis of the data included in the signal 33.

[Sensor Device]

Although the structure that can be worn on an eyeball of a human body is described in the above, a variety of embodiments can be used for the sensor device 12. Other examples of the sensor device 12 are described below.

Figure 3A:
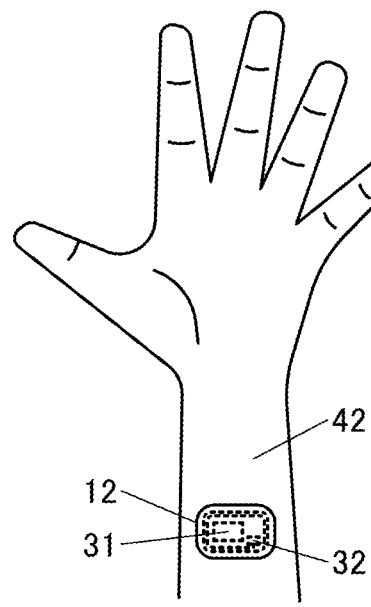
FIG. 3A to FIG. 3E are diagrams illustrating structure examples of a sensor device.

FIG. 3A illustrates the sensor device 12 that is attached to skin. FIG. 3A illustrates a state where the sensor device 12 is attached on an arm 42. The sensor device 12 includes the sensor portion 31 and the communication portion 32 each having a chip form. The exterior of the sensor device 12 is preferably a thin sheet-like member and preferably has flexibility or elasticity. The sensor device 12 can have a structure including an adhesive on the side of a surface in contact with the skin.

Figure 3B:
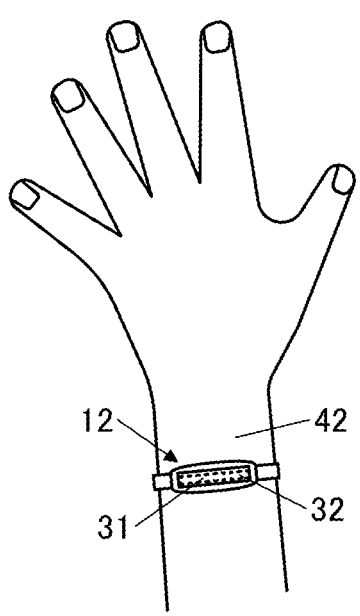

FIG. 3B illustrates the sensor device 12 that can wrap around the arm 42 (wrist). The sensor device 12 includes at least the sensor portion 31 and the communication portion 32. Furthermore, the sensor device 12 illustrated in FIG. 3B may include an information display portion, and for example, the sensor device 12 may function as a wrist-watch type information terminal.

Figure 3C:
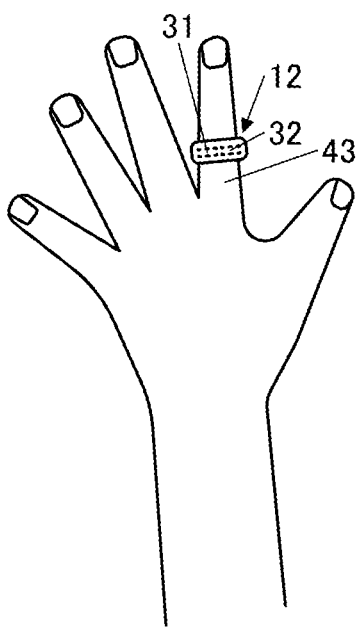

FIG. 3C illustrates the sensor device 12 that can be worn on a finger 43. The sensor device 12 illustrated in FIG. 3C includes at least the sensor portion 31 and the communication portion 32. The sensor device 12 may include an information display portion, and for example, the sensor device 12 may function as a ring type information terminal. Furthermore, the sensor device 12 may be an input device that has a structure including a gyroscope sensor or the like and thus uses gestures.

Figure 3D:
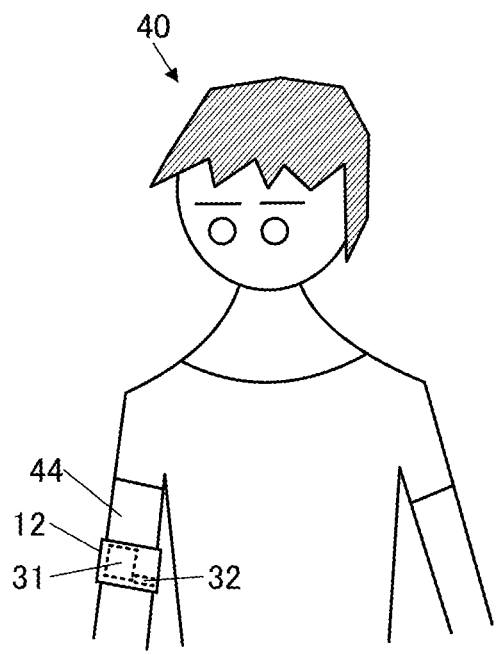

FIG. 3D illustrates the sensor device 12 that can be worn on an upper arm 44 of a user 40. The sensor device 12 includes at least the sensor portion 31 and the communication portion 32. The sensor device 12 preferably has a cylindrical exterior made of a material having elasticity or an exterior having a shape in which part of a cylinder is lacking (that is, the cross-sectional shape is a schematic C shape).

Figure 3E:
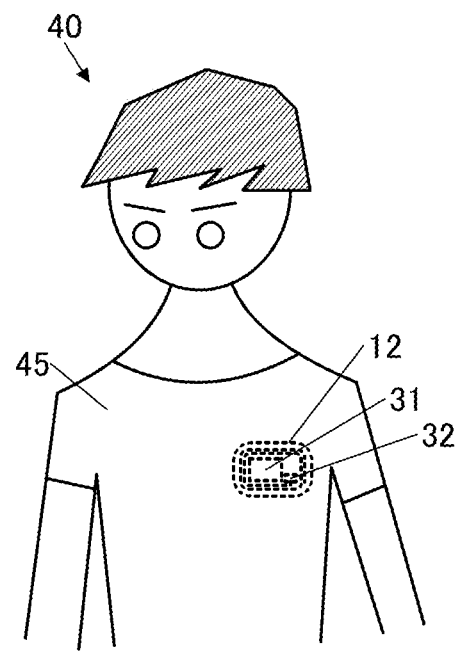

FIG. 3E illustrates the sensor device 12 that is fixed to the inner side of clothes 45 of the user 40. The sensor device 12 includes at least the sensor portion 31 and the communication portion 32. When the user 40 wears the clothes 45 on the innermost side, part of the sensor device 12 is preferably in contact with the skin. Even when the user 40 wears another clothes on the inner side of the clothes 45, it is preferable that the sensor device 12 can obtain the user's biological information through the other clothes. Note that the sensor device 12 may be fixed to the outer side of the clothes 45 or inside the clothes 45.

Here, the sensor device 12 preferably has a function of detecting at least one of a blood sugar level, a heart rate, a pulse, a blood pressure, a body temperature, a degree of oxygen saturation, and a neutral fat concentration. As described above, the blood sugar level can be estimated by measuring the concentration of glucose in a body fluid.

Moreover, reflectivity of an artery (arteriole) with respect to infrared light or visible light is changed in accordance with a change of a degree of blood oxygen saturation; thus, optical measurement of the artery can be performed. By obtaining this change over time, i.e., temporal modulation of a degree of blood oxygen saturation, information on the pulse wave can be obtained. Thus, the user's heart rate can be measured. Furthermore, with infrared light or visible light, the neutral fat concentration in blood, the glucose concentration in blood or a corium, or the like can be detected.

When a structure in which an electrode in contact with the skin is provided is used for the sensor portion 31, an electrocardiogram can be measured.

The blood pressure can be calculated from a difference in timing of two pulsations of the electrocardiogram and the pulse wave (a period of pulse wave propagation time), for example. A high blood pressure results in a short pulse wave propagation time, whereas a low blood pressure results in a long pulse wave propagation time. The body conditions of the user can be estimated from a relationship between the heart rate and the blood pressure that are calculated from the electrocardiogram and the pulse wave. For example, when both the heart rate and the blood pressure are high, it can be estimated that the user is nervous or excited, whereas when both the heart rate and the blood pressure are low, it can be estimated that the user is relaxed. When the state where the blood pressure is low and the heart rate is high is continued, the user might suffer from a heart disease or the like.

Note that it is preferable to provide a means of obtaining other biological information for the sensor device 12 or the display device 11. Examples of such biological information include internal biological information on an electrocardiogram, a blood pressure, a body temperature, and the like and superficial biological information on facial expression, a complexion, a pupil, and the like. In addition, information on the number of steps taken, exercise intensity, a height difference in a movement, and a meal (e.g., calorie intake and nutrients) are important for health care. The use of a plurality of kinds of biological information and the like enables complex management of physical conditions, leading to not only daily health management but also early detection of injuries and diseases.

The sensor device 12 may include a GPS (Global Positioning System) with which position information can be obtained. The sensor device 12 may have a function of electronic payment.

[Example of Image]

Examples of images that can be shown to a user by the composite device 10 are described below.

Figure 4A:
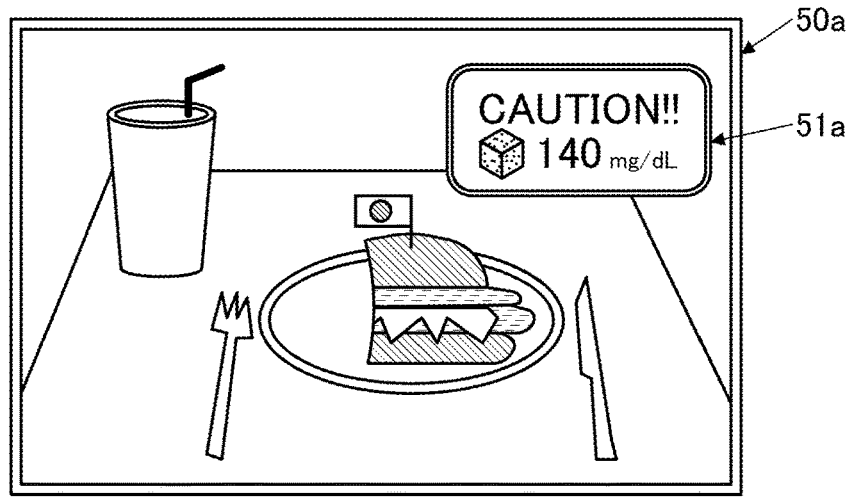
FIG. 4A to FIG. 4C are diagrams illustrating examples of an image.

FIG. 4A illustrates an example of an image 50a that is reflected on the field of vision of the user at meals. In the image 50a, image information 51a is superimposed on an actual image taken by the image capturing portion 23. In the image information 51a illustrated in FIG. 4A, an icon image that represents a blood sugar level (an image resembling a cube sugar), a comment for warning the user of a high blood sugar level, and an estimated blood sugar level are shown (CAUTION!! 140 mg/dL). The user notices that his/her blood sugar level is high from the image information 51a, and can take actions such as eating less, canceling the order of a dessert, or ordering a drink for inhibiting an increase in the blood sugar level.

Figure 4B:
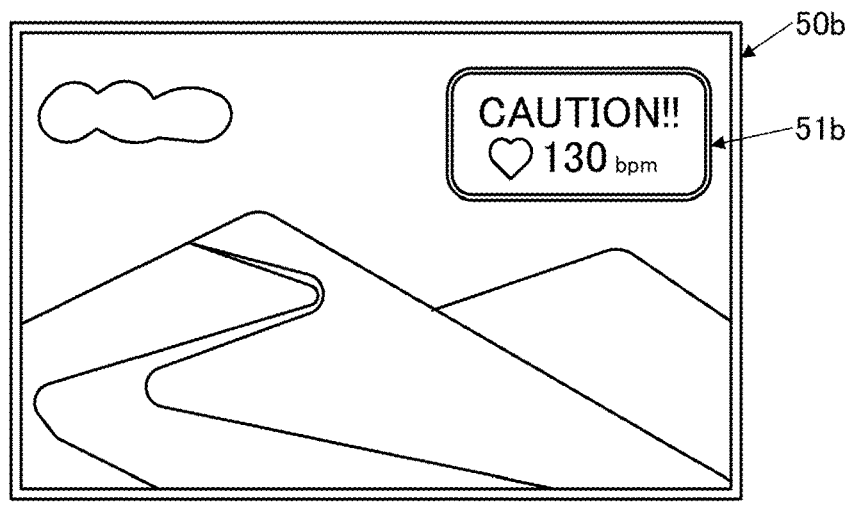

FIG. 4B illustrates an example of an image 50b that is reflected on the field of vision of the user who is hiking. Image information 51b is shown in the image 50b. In the image information 51b, an icon image that represents a heart rate (an image resembling a heart), a comment for warning the user of a high heart rate, and an estimated heart rate are shown (CAUTION!! 130 bpm). The user can notice that his/her heart rate is high from the image information 51b, and can take actions such as taking a rest or walking slowly.

Figure 4C:
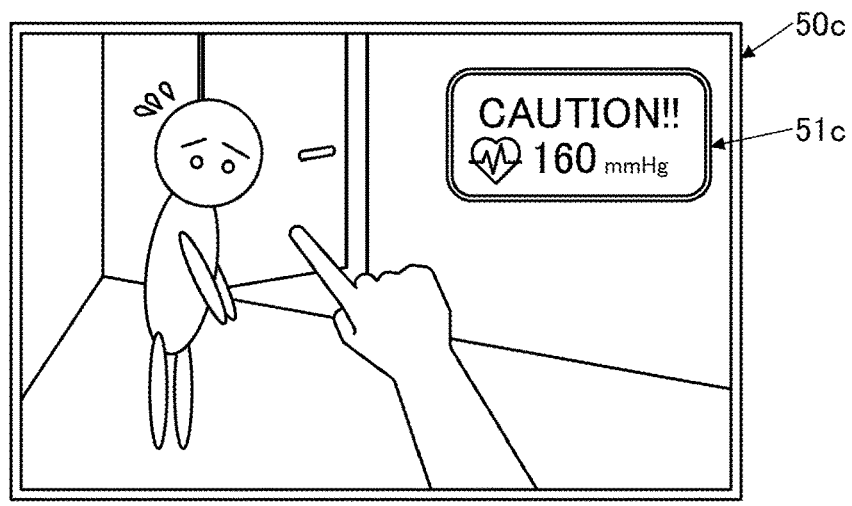

FIG. 4C illustrates an example of an image 50c that is reflected on the field of vision of the user who calls his/her subordinate and is reprimanding him/her. Image information 51c is shown in the image 50c. In the image information 51c, an icon image that represents a blood pressure (an image resembling a heart and an electrocardiogram), a comment for warning the user of a high blood pressure, and an estimated blood pressure are shown (CAUTION!! 160 mmHg). The user can notice that he or she is extremely excited from the image information 51c, and can take actions such as breathing deeply to quell his/her anger or reconsidering a way of communicating with his/her subordinate.

Although the examples in which the comments for warning the user are illustrated are shown in the above, display for urging the user to do a specific action may be performed. For example, in the situation shown in FIG. 4C, a comment for urging the user to breathe deeply, an animation image, or the like may be shown.

MODIFICATION EXAMPLE

Modification examples of the above structure example are described below.

Figure 5A:
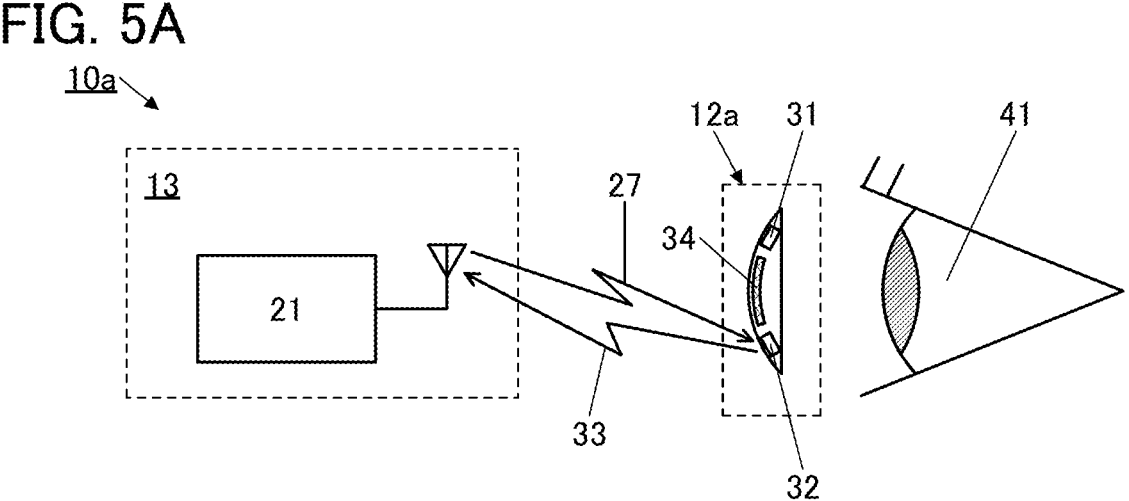
FIG. 5A and FIG. 5B are diagrams illustrating a structure example of a composite device.
Figure 5B:
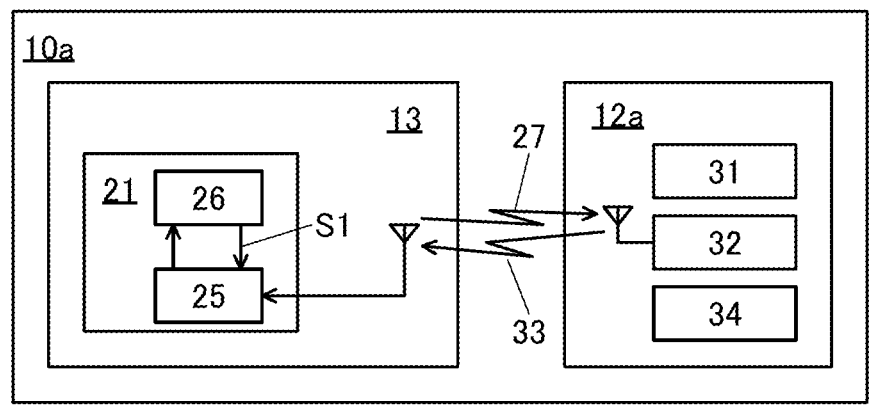

FIG. 5A is a schematic diagram of the composite device 10a, and FIG. 5B is a block diagram of the composite device 10a.

The composite device 10a includes the sensor device 12a having a function of displaying an image and an information processing device 13.

The sensor device 12a includes a display portion 34 in addition to the sensor portion 31 and the communication portion 32. The display portion 34 has a function of displaying an image. As the display portion 34, a see-through display can be favorably used.

The communication portion 32 has a function of transmitting the signal 33 including information obtained by the sensor portion 31 to the information processing device 13. Furthermore, the communication portion 32 has a function of demodulating a signal 27 received from the information processing device 13 and outputting an image signal included in the signal 27 to the display portion 34.

The display portion 34 can display an image on the basis of the image signal input from the communication portion 32.

The information processing device 13 includes the control portion 21. The control portion 21 includes the communication portion 25 and the image generation portion 26.

The communication portion 25 has a function of receiving the signal 33 transmitted from the sensor device 12a and outputting data included in the signal to the image generation portion 26. Moreover, the communication portion 25 has a function of transmitting the signal 27, which is input from the image generation portion 26 and includes the image signal S1, to the sensor device 12a.

When data included in the signal 33 is input from the communication portion 25, the image generation portion 26 has a function of generating the image signal S1 on the basis of the input data and outputting the image signal S1 to the communication portion 25.

The user can see an image displayed on the display portion 34 in a state where the image is superimposed on a transmission image that is transmitted through the sensor device 12a. The composite device 10a can show AR display to the user. Alternatively, a structure in which the display portion 34 does not transmit light may be employed to show VR display to the user.

With such a structure, the structure of the composite device 10a can be extremely simple. Furthermore, since the information processing device 13 is easily reduced in size and weight, the information processing device 13 can be put into a pocket or a bag. In that case, the composite device 10*a* does not bother the user since a device worn on a head is not required.

At least part of this embodiment can be implemented in combination with the other embodiments described in this specification as appropriate.

Embodiment 2

In this embodiment, structure examples of electronic devices each of which includes a display device and can be used for the composite device of one embodiment of the present invention are described.

Figure 6A:
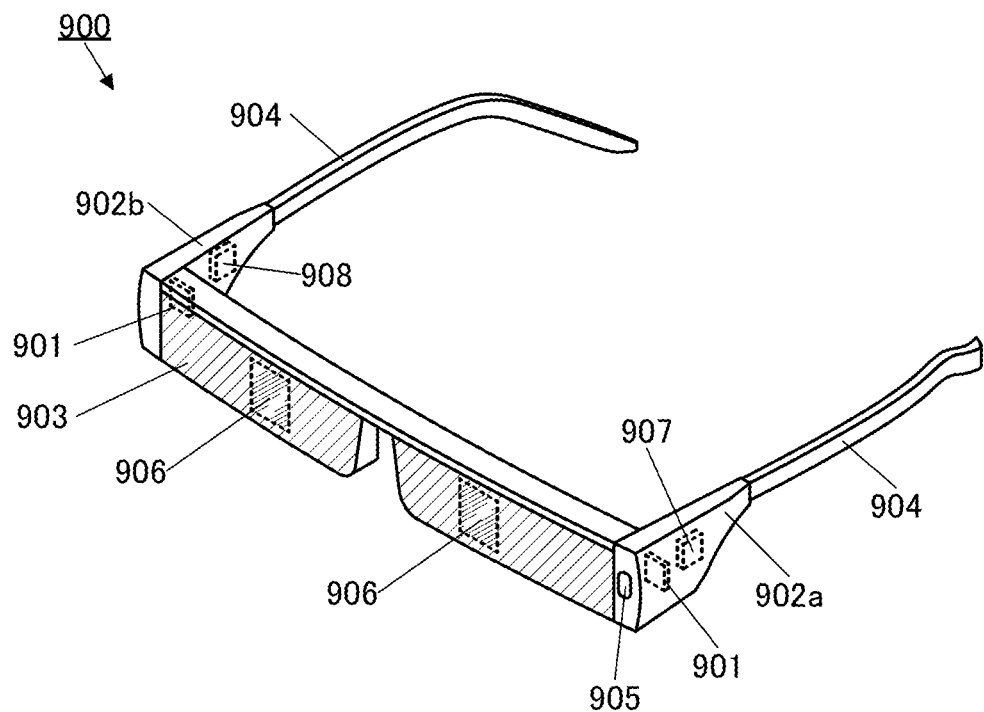
FIG. 6A and FIG. 6B are diagrams illustrating a structure example of an electronic device.

FIG. 6A is a perspective view of an electronic device 900 that is of a glasses type. The electronic device 900 includes a pair of display panels 901, a pair of housings (a housing 902*a* and a housing 902*b*), a pair of optical members 903, a pair of mounting portions 904, and the like.

The electronic device 900 can project an image displayed on the display panel 901 onto a display region 906 of the optical member 903. Since the optical members 903 have a light-transmitting property, a user can see images displayed on the display regions 906, which are superimposed on transmission images seen through the optical members 903. Thus, the electronic device 900 is an electronic device capable of AR display.

One housing 902*a* is provided with a camera 905 capable of capturing an image of what lies in front thereof. Furthermore, the housing 902*a* includes a wireless communication device 907, and a video signal or the like can be supplied to the housing 902*a* and the housing 902*b*. Instead of or in addition to the wireless communication device 907, a connector that can be connected to a cable for supplying a video signal or a power supply potential may be provided. Furthermore, when the housing 902*a* or the housing 902*b* is provided with an acceleration sensor such as a gyroscope sensor, the orientation of the user's head can be detected and an image corresponding to the orientation can be displayed on the display region 906. Moreover, the housing 902*a* or the housing 902*b* is preferably provided with a battery, in which case charging can be performed with or without a wire.

Furthermore, the housing 902*b* includes a processor 908. The processor 908 has a function of controlling the components of the electronic device 900, such as the camera 905, the wireless communication device 907, and the pair of display panels 901, a function of generating an image, and the like. The processor 908 may have a function of generating a synthesized image for AR display.

Data communication with an external device can be performed by the wireless communication device 907. For example, when data transmitted from the outside is output to the processor 908, the processor 908 can generate image data for AR display on the basis of the transmitted data. Examples of the data transmitted from the outside include, in addition to image data, data including biological information transmitted from a biological sensor device or the like.

Next, a method for projecting an image on the display region 906 of the electronic device 900 is described with reference to FIG. 6B. The display panel 901, a lens 911, and a reflective plate 912 are provided in a housing 902 (the housing 902*a* and the housing 902*b*). A reflective surface 913 functioning as a half mirror is provided in a portion corresponding to the display region 906 of the optical member 903.

Light 915 emitted from the display panel 901 passes through the lens 911 and is reflected by the reflective plate 912 to the optical member 903 side. In the optical member 903, the light 915 is fully reflected repeatedly by end surfaces of the optical member 903 and reaches the reflective surface 913, whereby an image is projected on the reflective surface 913. Accordingly, the user can see both the light 915 reflected by the reflective surface 913 and transmitted light 916 that has passed through the optical member 903 (including the reflective surface 913).

Figure 6B:
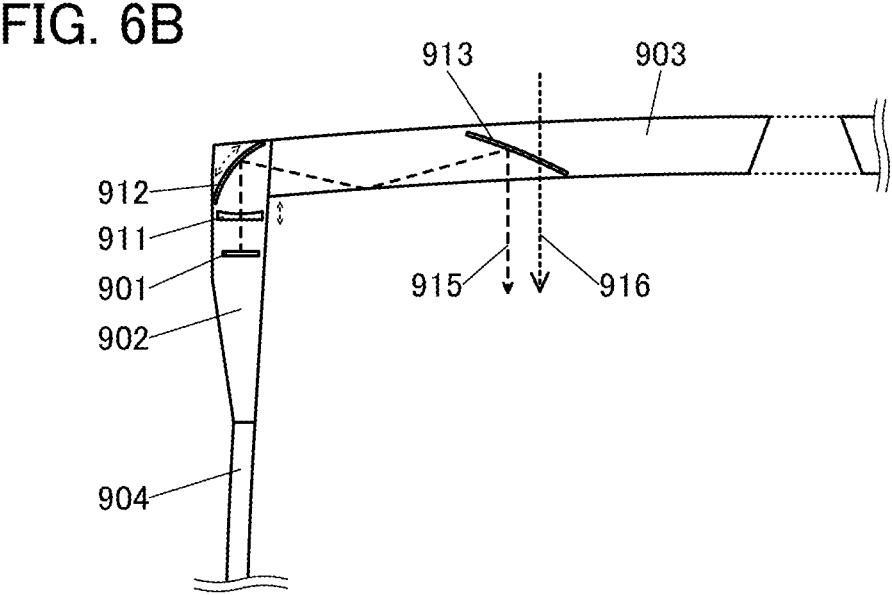

FIG. 6B shows an example in which a surface of the reflective plate 912 and the reflective surface 913 each have a curved surface. This can increase optical design flexibility and reduce the thickness of the optical member 903, compared to the case where they have flat surfaces. Note that the surface of the reflective plate 912 and the reflective surface 913 may have flat surfaces.

The reflective plate 912 can use a component having a mirror surface, and preferably has high reflectivity. As the reflective surface 913, a half mirror utilizing reflection of a metal film may be used, but the use of a prism utilizing total reflection or the like can increase the transmittance of the transmitted light 916.

Here, the housing 902 preferably includes a mechanism for adjusting the distance and angle between the lens 911 and the display panel 901. This enables focus adjustment, zooming in/out of an image, or the like. One or both of the lens 911 and the display panel 901 are configured to be movable in the optical-axis direction, for example.

The housing 902 preferably includes a mechanism capable of adjusting the angle of the reflective plate 912. The position of the display region 906 where images are displayed can be changed by changing the angle of the reflective plate 912. Thus, the display region 906 can be placed at the optimal position in accordance with the position of the user's eye.

The display device or the display module of one embodiment of the present invention can be used for the display panel 901. Thus, the electronic device 900 can perform display with extremely high resolution.

Figure 7A:
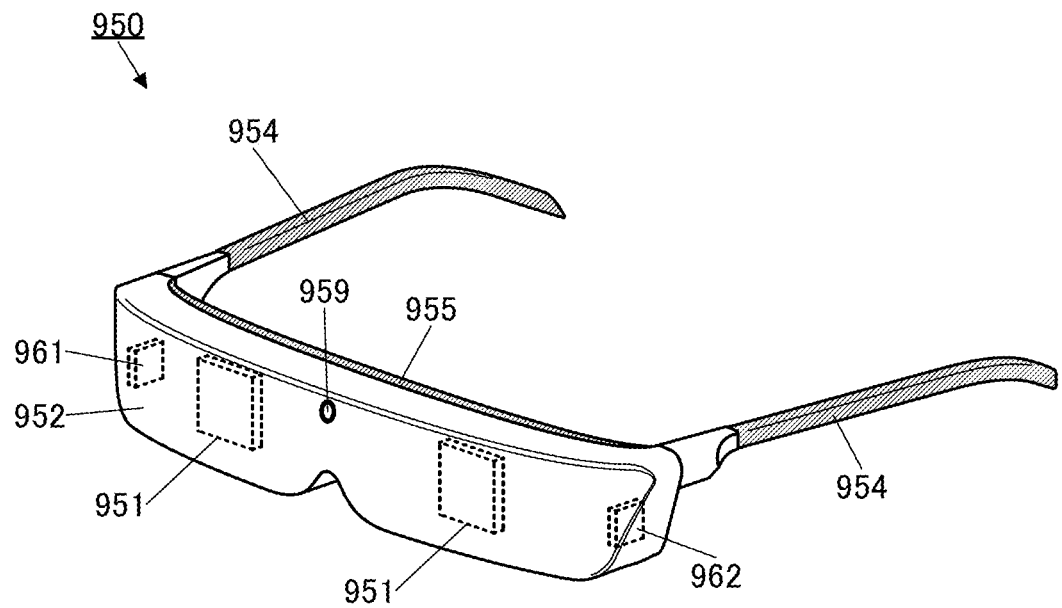
FIG. 7A and FIG. 7B are diagrams illustrating a structure example of an electronic device.
Figure 7B:
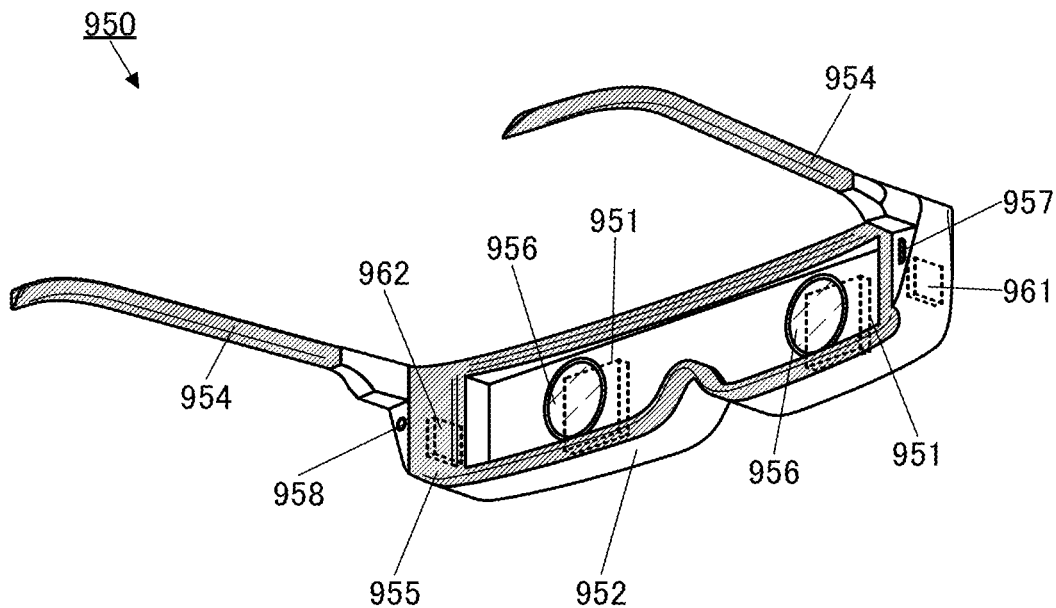

FIG. 7A and FIG. 7B illustrate perspective views of a goggle-type electronic device 950. FIG. 7A is a perspective view illustrating the front surface, the top surface, and the left side surface of the electronic device 950, and FIG. 7B is a perspective view illustrating the back surface, the bottom surface, and the right side surface of the electronic device 950.

The electronic device 950 includes a pair of display panels 951, a housing 952, a pair of mounting portions 954, a cushion 955, a pair of lenses 956, and the like. The pair of display panels 951 is positioned to be seen through the lenses 956 inside the housing 952.

The electronic device 950 is an electronic device for VR. A user wearing the electronic device 950 can see an image displayed on the display panels 951 through the lenses 956. Furthermore, when the pair of display panels 951 displays different images, three-dimensional display using parallax can be performed. Furthermore, the housing 952 included in the electronic device 950 may be provided with a waterproof function so that the electronic device 950 can be used also in the water. In that case, it is preferable to make the housing 952 have a streamlined shape, in which case water resistance can be reduced and thus the user can swim faster.

An input terminal 957 and an output terminal 958 are provided on the back surface side of the housing 952. To the input terminal 957, a cable for supplying a video signal from a video output device or the like, power for charging a battery provided in the housing 952, or the like can be connected. The output terminal 958 can function as, for example, an audio output terminal to which earphones, headphones, or the like can be connected. Note that in the case where audio data can be output by wireless communication or sound is output from an external video output device, the audio output terminal is not necessarily provided.

The housing 952 is provided with a camera 959 capable of taking an image of what lies in front thereof. The electronic device 950 can display an image taken by the camera 959 or a synthesized image using the image. The electronic device 950 can perform AR display and MR display in addition to VR display.

Furthermore, a processor 961 and a wireless communication device 962 are provided in the housing 952. The processor 961 can control the components of the electronic device 950, such as a pair of display panels 951, the camera 959, the wireless communication device 962, and the like. In addition, the processor 961 can form an image to be displayed on the display panel 951.

Furthermore, data communication with an external device can be performed by the wireless communication device 962. For example, when data transmitted from the outside is output to the processor 961, the processor 961 can generate image data for VR display, AR display, or MR display on the basis of the transmitted data. Examples of the data transmitted from the outside include, in addition to image data, data including biological information transmitted from a biological sensor device or the like.

In addition, the housing 952 preferably includes a mechanism by which the left and right positions of the lenses 956 and the display panels 951 can be adjusted to the optimal positions in accordance with the positions of the user's eyes. In addition, a mechanism for adjusting focus by change in the distance between the lens 956 and the display panel 951 is preferably included.

The display device or the display module of one embodiment of the present invention can be used for the display panel 951. Thus, the electronic device 950 can perform display with extremely high resolution. This enables a user to feel high sense of immersion.

The cushion 955 is a portion in contact with the user's face (forehead, cheek, or the like). The cushion 955 is in close contact with the user's face, so that light leakage can be prevented, which further increases the sense of immersion. A soft material is preferably used for the cushion 955 so that the cushion 955 is in close contact with the user's face when the user wears the electronic device 950. For example, a material such as rubber, silicone rubber, urethane, or sponge can be used. Furthermore, when a sponge or the like whose surface is covered with cloth, leather (natural leather or synthetic leather), or the like is used, a gap is unlikely to be generated between the user's face and the cushion 955, whereby light leakage can be suitably prevented. Furthermore, using such a material is preferable because it has a soft texture and the user does not feel cold when wearing the device in a cold season, for example. The member in contact with user's skin, such as the cushion 955 or the mounting portion 954, is preferably detachable, in which case cleaning or replacement can be easily performed.

At least part of this embodiment can be implemented in combination with the other embodiments described in this specification as appropriate.

Embodiment 3

In this embodiment, a structure example of a display panel that can be applied to the composite device according to one embodiment of the present invention is described. The display panel described below as an example can have extremely high resolution and thus can be favorably used for a display device or a display portion included in a sensor device.

[Pixel Structure Example]

An example of a pixel layout suitable for a high-resolution display panel is described below.

For example, a structure shown below enables a display device where pixels including light-emitting elements are arranged in a display region at a resolution (pixel density) higher than or equal to 1000 ppi and less than or equal to 50000 ppi, preferably higher than or equal to 2000 ppi and less than or equal to 20000 ppi, further preferably higher than or equal to 3000 ppi and less than or equal to 10000 ppi, still further preferably higher than or equal to 5000 ppi and less than or equal to 10000 ppi. Typically, the pixel density can be higher than or equal to 4500 ppi and less than or equal to 5500 ppi, higher than or equal to 5500 ppi and less than or equal to 6500 ppi, or higher than or equal to 6500 ppi and less than or equal to 7500 ppi

[Structure Example of Pixel Circuit]

Figure 8A:
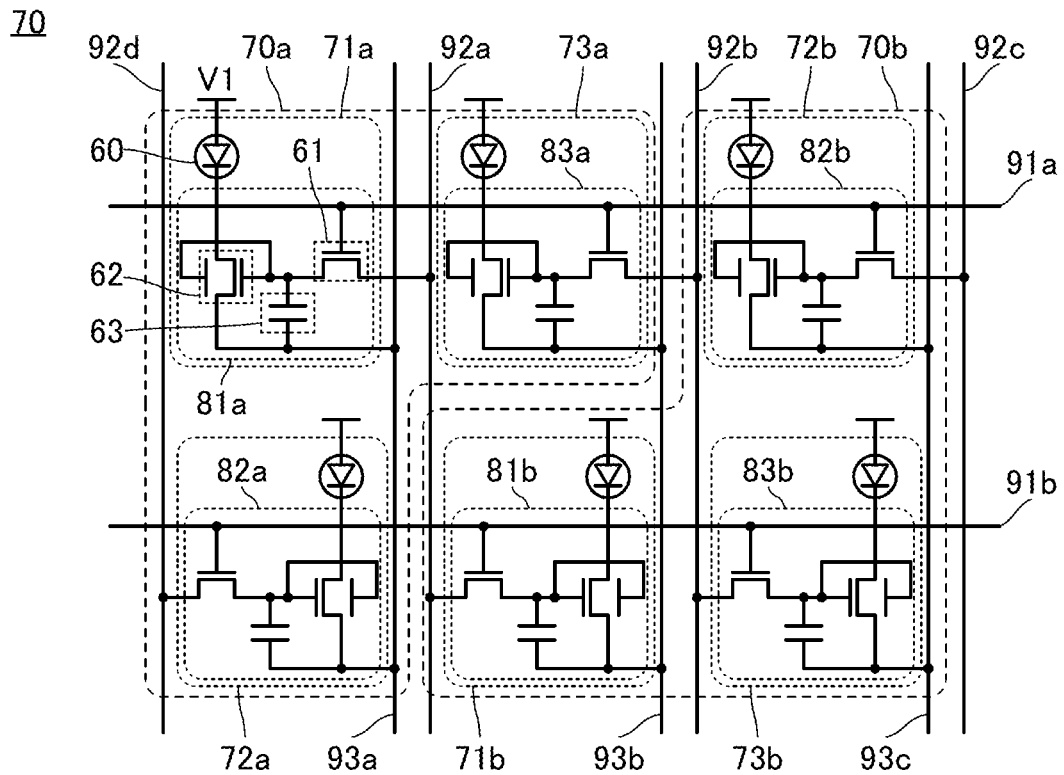
FIG. 8A and FIG. 8B are diagrams illustrating a structure example of a display panel.

FIG. 8A shows an example of a circuit diagram of a pixel unit 70. The pixel unit 70 is composed of two pixels (a pixel 70a and a pixel 70b). In addition, the pixel unit 70 is connected to a wiring 91a, a wiring 91b, a wiring 92a, a wiring 92b, a wiring 92c, a wiring 92d, a wiring 93a, a wiring 93b, a wiring 93c and the like.

The pixel 70a includes a subpixel 71a, a subpixel 72a, and a subpixel 73a. The pixel 70b includes a subpixel 71b, a subpixel 72b, and a subpixel 73b. The subpixel 71a, the subpixel 72a, and the subpixel 73a include a pixel circuit 81a, a pixel circuit 82a, and a pixel circuit 83a, respectively. The subpixel 71b, the subpixel 72b, and the subpixel 73b include a pixel circuit 81b, a pixel circuit 82b, and a pixel circuit 83b, respectively.

Each subpixel includes the pixel circuit and a display element 60. For example, the subpixel 71a includes the pixel circuit 81a and the display element 60. A light-emitting element such as an organic EL element is used here as the display element 60.

The wiring 91a and the wiring 91b each have a function as a scan line (also referred to as a gate line). The wiring 92a, the wiring 92b, the wiring 92c, and the wiring 92d each have a function as a signal line (also referred to as a source line or a data line). The wiring 93a, the wiring 93b, and the wiring 93c each have a function of supplying a potential to the display element 60.

The pixel circuit 81a is electrically connected to the wiring 91a, the wiring 92a, and the wiring 93a. The pixel circuit 82a is electrically connected to the wiring 91b, the wiring 92d, and the wiring 93a. The pixel circuit 83a is electrically connected to the wiring 91a, the wiring 92b, and the wiring 93b. The pixel circuit 81b is electrically connected to the wiring 91b, the wiring 92a, and the wiring 93b. The pixel circuit 82b is electrically connected to the wiring 91a, the wiring 92c, and the wiring 93c. The pixel circuit 83b is electrically connected to the wiring 91b, the wiring 92b, and the wiring 93c.

With the structure shown in FIG. 8A in which two gate lines are connected to one pixel, the number of source lines can be conversely reduced by half as compared with that in stripe arrangement. As a result, the number of ICs used as source driver circuits can be reduced by half and the number of components can be reduced.

One wiring functioning as a signal line is preferably connected to pixel circuits corresponding to the same color.

For example, when a signal with an adjusted potential is supplied to the wiring to correct for variation in luminance between pixels, the correction value may greatly vary between colors. Thus, when pixel circuits connected to one signal line are pixel circuits corresponding to the same color, the correction can be performed easily.

In addition, each pixel circuit includes a transistor 61, a transistor 62, and a capacitor 63. In the pixel circuit 81*a*, for example, a gate of the transistor 61 is electrically connected to the wiring 91*a*, one of a source and a drain of the transistor 61 is electrically connected to the wiring 92*a*, and the other of the source and the drain is electrically connected to a gate of the transistor 62 and one electrode of the capacitor 63. One of a source and a drain of the transistor 62 is electrically connected to one electrode of the display element 60, and the other of the source and the drain is electrically connected to the other electrode of the capacitor 63 and the wiring 93*a*. The other electrode of the display element 60 is electrically connected to a wiring to which a potential V1 is applied.

Note that, as shown in FIG. 8A, the other pixel circuits are similar to the pixel circuit 81*a* except that any of the wiring to which the gate of the transistor 61 is connected, the wiring to which the one of the source and the drain of the transistor 61 is connected, and the wiring to which the other electrode of the capacitor 63 is connected is different between the pixel circuit 81*a* and the other pixel circuits.

In FIG. 8A, the transistor 61 serves as a selection transistor. The transistor 62 is in a series connection with the display element 60 and has a function of controlling a current flowing into the display element 60. The capacitor 63 has a function of holding the potential of a node connected to the gate of the transistor 62. Note that the capacitor 63 does not have to be intentionally provided in the case where an off-state leakage current of the transistor 61, a leakage current through the gate of the transistor 62, and the like are extremely small.

The transistor 62 preferably includes a first gate and a second gate electrically connected to each other as shown in FIG. 8A. This structure with the two gates can increase the amount of current that the transistor 62 can carry. Such a structure is particularly preferable for a high-resolution display device because the amount of current can be increased without increasing the size, the channel width in particular, of the transistor 62.

Note that the transistor 62 may have one gate. This structure eliminates the need for forming the second gate and thus can simplify the process as compared with the above structure. The transistor 61 may have two gates. This structure enables a reduction in size of each transistor. A first gate and a second gate of each transistor can be electrically connected to each other. Alternatively, one gate may be electrically connected to a different wiring. In this case, threshold voltages of the transistors can be controlled by varying potentials that are applied to the wirings.

One of a pair of electrodes of the display element 60 that is electrically connected to the transistor 62 corresponds to a pixel electrode. FIG. 8A shows a structure where an electrode of the display element 60 that is electrically connected to the transistor 62 is a cathode and the opposite electrode is an anode. This structure is particularly effective when the transistor 62 is an n-channel transistor. That is, when the transistor 62 is on, the potential applied by the wiring 93*a* is a source potential; accordingly, the amount of current flowing into the transistor 62 can be constant regardless of variation or change in resistance of the display element 60. Alternatively, a p-channel transistor may be used as a transistor of the pixel circuit.

[Structure Example of Display Element]

Figure 8B:
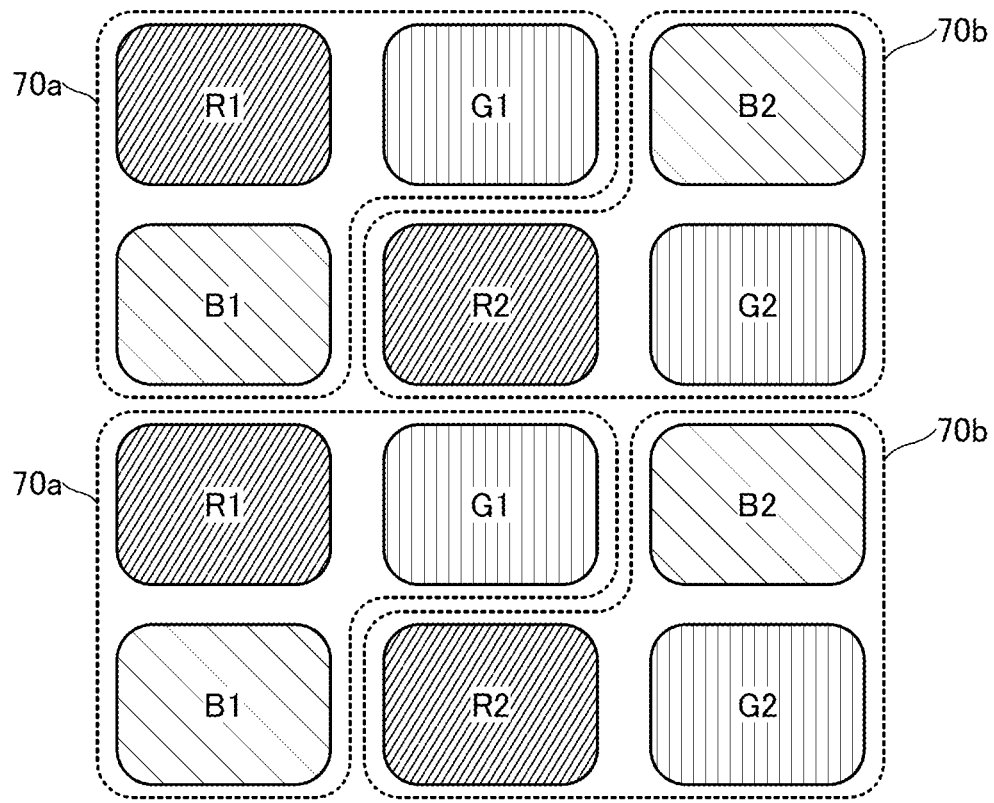

FIG. 8B is a schematic top view illustrating an example of a layout of display elements. FIG. 8B is a schematic top view of two pixel units.

The pixel 70*a* includes a display element R1, a display element G1, and a display element B1. The pixel 70*b* includes a display element R2, a display element G2, and a display element B2. The display element R1 and the display element R2 exhibit a red color, the display element G1 and the display element G2 exhibit a green color, and the display element B1 and the display element B2 exhibit a blue color.

As the arrangement of the display element R1 and the display element R2, they are arranged in a zigzag line in the longitudinal direction. Similarly, the display element G1 and the display element G2 are also arranged in a zigzag line, and the display element B1 and the display element B2 are also arranged in a zigzag line. With such a structure, the viewing angle dependence is improved, which brings an effect that deviation of chromaticity or luminance is less likely to occur when the device is seen from an oblique direction with respect to the display surface.

The above is the description of the structure examples of the pixels.

[Structure Example of Display Module]

A structure example of a display module of one embodiment of the present invention is described below.

Figure 9A:
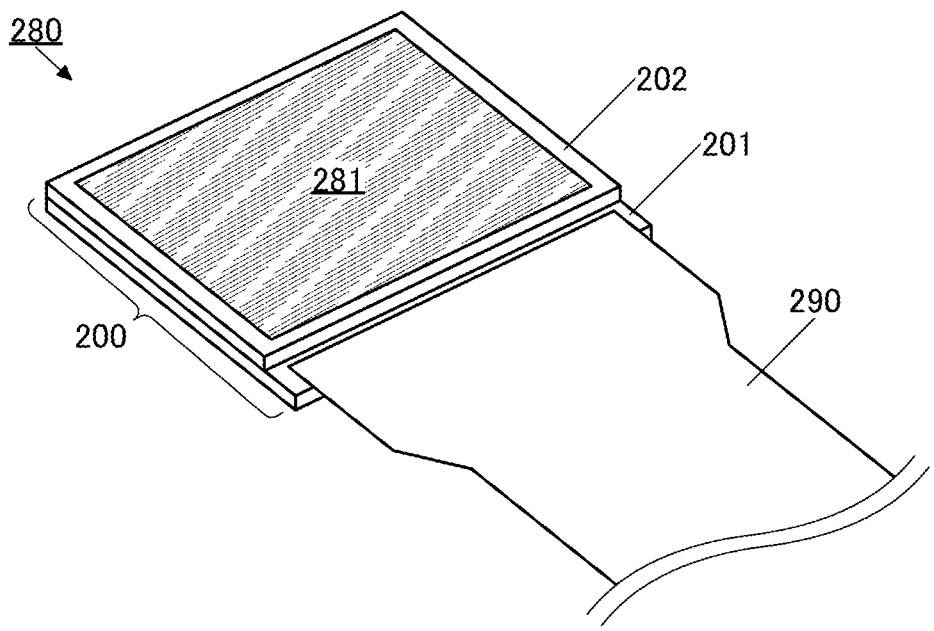
FIG. 9A and FIG. 9B are diagrams illustrating structure examples of a display module.

FIG. 9A is a schematic perspective view of a display module 280. The display module 280 includes a display device 200 and an FPC 290.

The display module 280 includes the substrate 201 and the substrate 202. A display portion 281 is also included on the substrate 202 side. The display portion 281 is a region of the display module 280 where an image is displayed and is a region where light emitted from pixels provided in a pixel portion 284 described later can be seen.

Figure 9B:
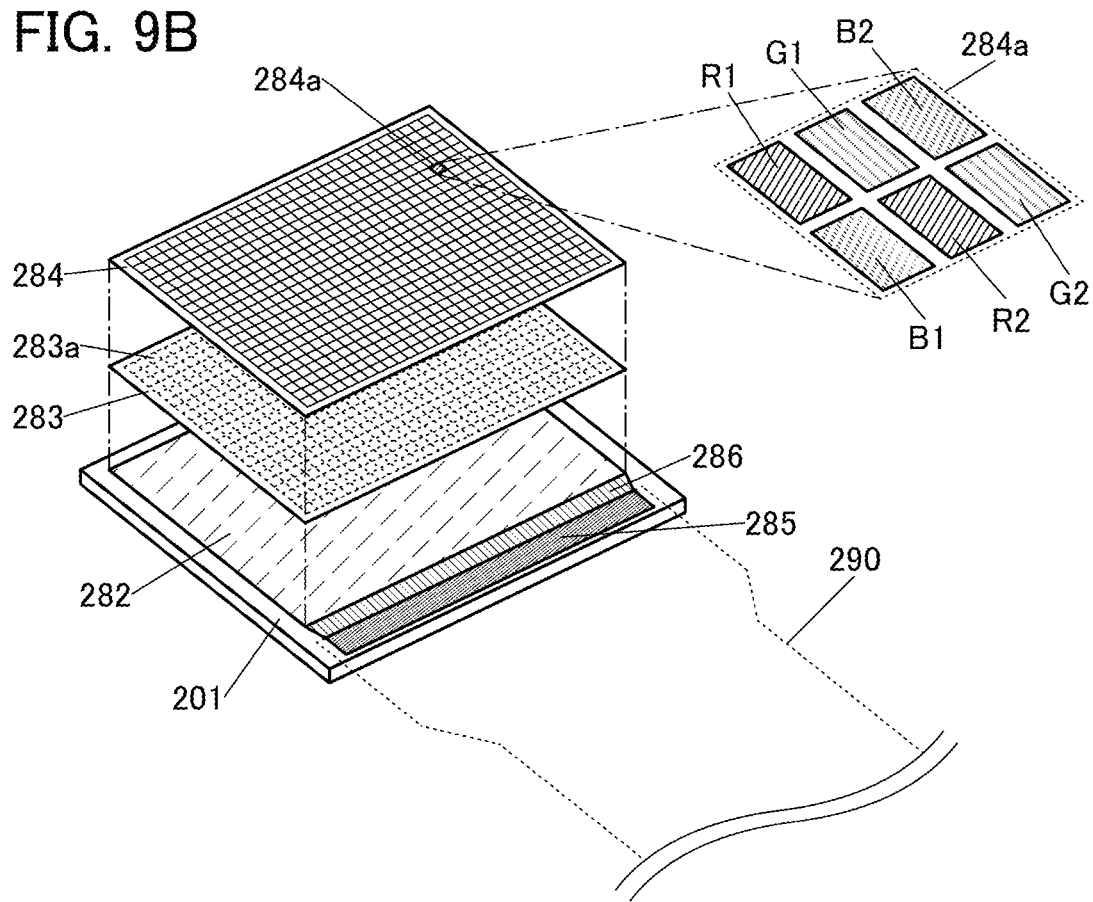

FIG. 9B illustrates a perspective view schematically illustrating a structure on the substrate 201 side. The substrate 201 has a structure in which a circuit portion 282, a pixel circuit portion 283 over the circuit portion 282, and the pixel portion 284 over the pixel circuit portion 283 are stacked. In addition, a terminal portion 285 for connection to the FPC 290 is included in a portion not overlapping with the pixel portion 284 over the substrate 201. The terminal portion 285 and the circuit portion 282 are electrically connected to each other through a wiring portion 286 formed of a plurality of wirings.

The pixel portion 284 includes a plurality of pixels 284*a* arranged in a matrix. An enlarged view of one pixel 284*a* is illustrated on the right side of FIG. 9B. The pixel 284*a* includes the display element R1, the display element G1, the display element B1, the display element R2, the display element G2, and the display element B2. The pixel 284*a* corresponds to the pixel unit 70 that is described above with reference to FIG. 8A and FIG. 8B as an example.

The pixel circuit portion 283 includes a plurality of pixel circuits 283*a* arranged in a matrix. One pixel circuit 283*a* is a circuit that controls light emission of six display elements included in one pixel 284*a*. One pixel circuit 283*a* may be provided with six circuits for controlling light emission of respective display elements. For example, the pixel circuit 283*a* for one display element can include at least one selection transistor, one current control transistor (driving transistor), and a capacitor. In this case, a gate signal is input to a gate of the selection transistor and a source signal is input to one of a source and a drain thereof. With such a structure, an active-matrix display device is achieved.

The circuit portion 282 includes a circuit for driving the pixel circuits 283a in the pixel circuit portion 283. For example, a gate line driver circuit and a source line driver circuit are preferably included. In addition, an arithmetic circuit, a memory circuit, a power supply circuit, or the like may be included.

The FPC 290 functions as a wiring for supplying a video signal or a power supply potential to the circuit portion 282 from the outside. In addition, an IC may be mounted on the FPC 290.

The display module 280 can have a structure in which the pixel circuit portion 283, the circuit portion 282, and the like are stacked below the pixel portion 284; thus, the aperture ratio (the effective display area ratio) of the display portion 281 can be significantly high. For example, the aperture ratio of the display portion 281 can be greater than or equal to 40% and less than 100%, preferably greater than or equal to 50% and less than or equal to 95%, and further preferably greater than or equal to 60% and less than or equal to 95%. Furthermore, the pixels 284a can be arranged extremely densely and thus the display portion 281 can have extremely high resolution. For example, in the display portion 281, the pixels 284a are preferably arranged with a resolution (pixel density) higher than or equal to 1000 ppi and less than or equal to 50000 ppi, preferably higher than or equal to 2000 ppi and less than or equal to 20000 ppi, further preferably higher than or equal to 3000 ppi and less than or equal to 10000 ppi, still further preferably higher than or equal to 5000 ppi and less than or equal to 10000 ppi. Typically, the pixel density can be higher than or equal to 4500 ppi and less than or equal to 5500 ppi, higher than or equal to 5500 ppi and less than or equal to 6500 ppi, or higher than or equal to 6500 ppi and less than or equal to 7500 ppi.

Such a display module 280 has extremely high resolution, and thus can be suitably used for a device for VR such as a head-mounted display or a glasses-type device for AR. For example, even in the case of a structure in which the display portion of the display module 280 is seen through a lens, pixels of the extremely-high-resolution display portion 281 included in the display module 280 are prevented from being seen when the display portion is enlarged by the lens, so that display providing a high sense of immersion can be performed. Without limitation to the above, the display module 280 can also be suitably used for an electronic device having a relatively small display portion. For example, the display module 280 can also be suitably used for a display portion of a wearable electronic device such as a wrist-watch type electronic device.

At least part of this embodiment can be implemented in combination with the other embodiments described in this specification as appropriate.

Embodiment 4

In this embodiment, an example of a CPU to which the composite system of one embodiment of the present invention can be applied is described. The CPU described below as an example can be favorably used especially for a control portion included in a display device.

<Structure of CPU>

Figure 10:
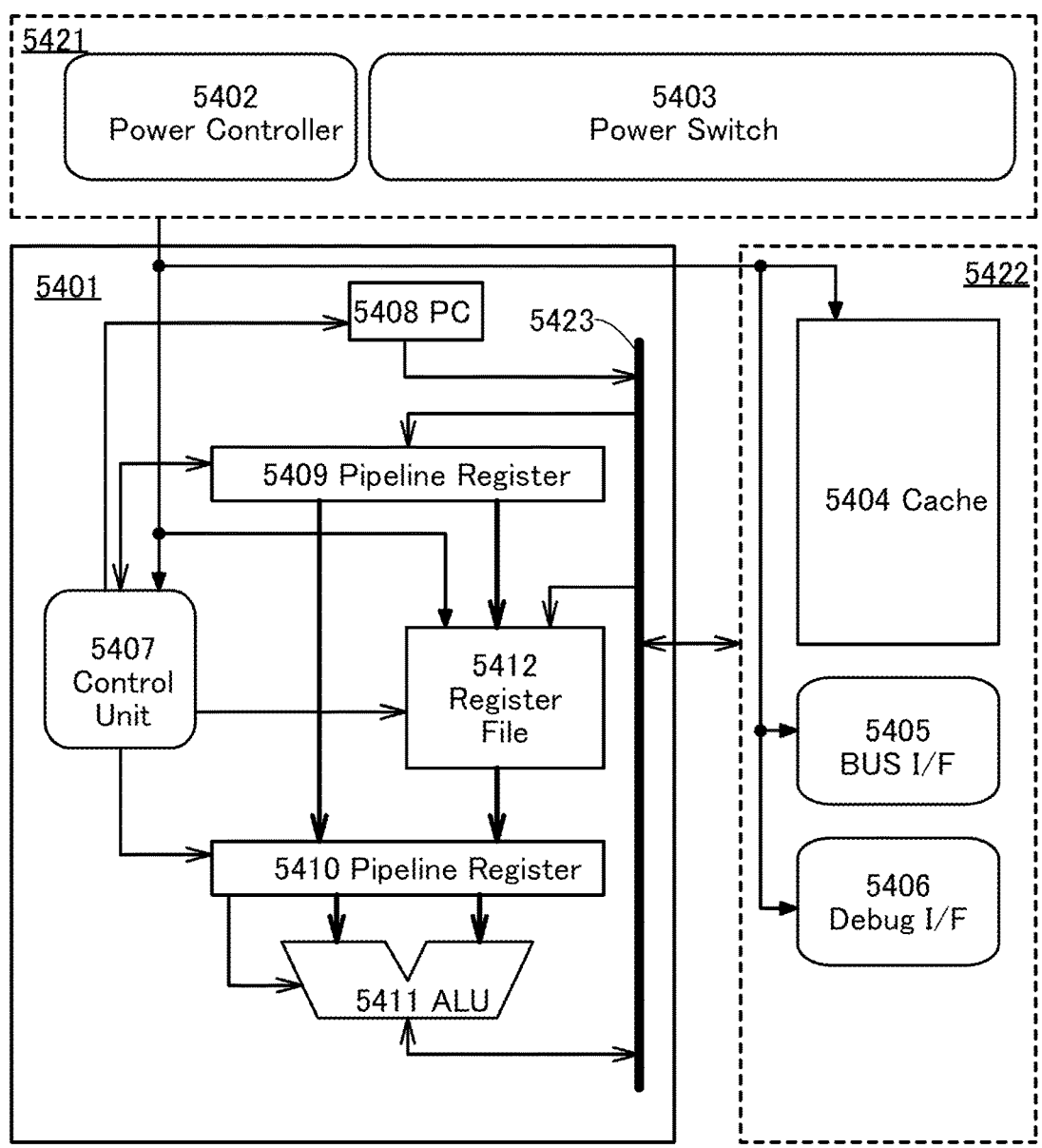
FIG. 10 is a diagram illustrating a structure example of a semiconductor device.

A semiconductor device 5400 shown in FIG. 10 includes a CPU core 5401, a power management unit 5421, and a peripheral circuit 5422. The power management unit 5421 includes a power controller 5402 and a power switch 5403. The peripheral circuit 5422 includes a cache 5404 including a cache memory, a bus interface (BUS I/F) 5405, and a debug interface (Debug I/F) 5406. The CPU core 5401 includes a data bus 5423, a control unit 5407, a PC (program counter) 5408, a pipeline register 5409, a pipeline register 5410, an ALU (Arithmetic logic unit) 5411, and a register file 5412. Data is transmitted between the CPU core 5401 and the peripheral circuit 5422 such as the cache 5404 via the data bus 5423.

The semiconductor device (cell) can be used for many logic circuits typified by the power controller 5402 and the control unit 5407. The semiconductor device (cell) can be used particularly for all logic circuits that can be constituted using standard cells. Accordingly, the semiconductor device 5400 can be small. The semiconductor device 5400 can have reduced power consumption. The semiconductor device 5400 can have a higher operating speed. The semiconductor device 5400 can have a smaller power supply voltage variation.

When p-channel Si transistors and the transistor described in the above embodiment which includes an oxide semiconductor (preferably an oxide containing In, Ga, and Zn) in a channel formation region are used in the semiconductor device (cell) and the semiconductor device (cell) is used in the semiconductor device 5400, the semiconductor device 5400 can be small. The semiconductor device 5400 can have reduced power consumption. The semiconductor device 5400 can have a higher operating speed. Particularly when the Si transistors are only p-channel ones, the manufacturing cost can be reduced.

The control unit 5407 has functions of decoding and executing instructions contained in a program such as input applications by controlling the overall operations of the PC 5408, the pipeline register 5409, the pipeline register 5410, the ALU 5411, the register file 5412, the cache 5404, the bus interface 5405, the debug interface 5406, and the power controller 5402.

The ALU 5411 has a function of performing a variety of arithmetic operations such as four arithmetic operations and logic operations.

The cache 5404 has a function of temporarily storing frequently used data. The PC 5408 is a register having a function of storing an address of an instruction to be executed next. Note that although not shown in FIG. 10, the cache 5404 is provided with a cache controller for controlling the operation of the cache memory.

The pipeline register 5409 has a function of temporarily storing instruction data.

The register file 5412 includes a plurality of registers including a general-purpose register and can store data that is read from the main memory, data obtained as a result of arithmetic operations in the ALU 5411, or the like.

The pipeline register 5410 has a function of temporarily storing data used for arithmetic operations in the ALU 5411, data obtained as a result of arithmetic operations in the ALU 5411, or the like.

The bus interface 5405 functions as a path for data between the semiconductor device 5400 and various devices outside the semiconductor device 5400. The debug interface 5406 functions as a path of a signal for inputting an instruction to control debugging to the semiconductor device 5400.

The power switch 5403 has a function of controlling supply of a power supply voltage to various circuits included in the semiconductor device 5400 other than the power controller 5402. The above various circuits belong to several different power domains. The power switch 5403 controls whether the power supply voltage is supplied to the various circuits in the same power domain. In addition, the power controller 5402 has a function of controlling the operation of the power switch 5403.

The semiconductor device 5400 having the above structure can perform power gating. An example of the power gating operation sequence is described.

First, by the CPU core 5401, timing for stopping the supply of the power supply voltage is set in a register of the power controller 5402. Then, an instruction of starting power gating is sent from the CPU core 5401 to the power controller 5402. Then, various registers and the cache 5404 included in the semiconductor device 5400 start data saving. Then, the power switch 5403 stops the supply of the power supply voltage to the various circuits included in the semiconductor device 5400 other than the power controller 5402. Then, an interrupt signal is input to the power controller 5402, whereby the supply of the power supply voltage to the various circuits included in the semiconductor device 5400 is started. Note that a counter may be provided in the power controller 5402 to be used to determine the timing of starting the supply of the power supply voltage regardless of input of an interrupt signal. Next, the various registers and the cache 5404 start data restoration. Then, execution of an instruction is resumed in the control unit 5407.

Such power gating can be performed in the whole processor or one or a plurality of logic circuits included in the processor. Furthermore, power supply can be stopped even for a short time. Consequently, power consumption can be reduced at a fine spatial or temporal granularity.

In performing power gating, data retained by the CPU core 5401 or the peripheral circuit 5422 is preferably saved in a short time. In that case, the power can be turned on or off in a short time, and an effect of saving power becomes significant.

In order that the data retained by the CPU core 5401 or the peripheral circuit 5422 be saved in a short time, the data is preferably saved in a flip-flop circuit itself (referred to as a flip-flop circuit capable of backup operation). Furthermore, the data is preferably saved in an SRAM cell itself (referred to as an SRAM cell capable of backup operation). The flip-flop circuit and SRAM cell that are capable of backup operation preferably include transistors including an oxide semiconductor (preferably an oxide containing In, Ga, and Zn) in a channel formation region. Consequently, the transistor has a low off-state current; thus, the flip-flop circuit and SRAM cell that are capable of backup operation can retain data for a long time without power supply. When the transistor has a high switching speed, the flip-flop circuit and SRAM cell that are capable of backup operation can save and restore data in a short time in some cases.

An example of the flip-flop circuit capable of backup operation is described with reference to FIG. 11.

Figure 11:
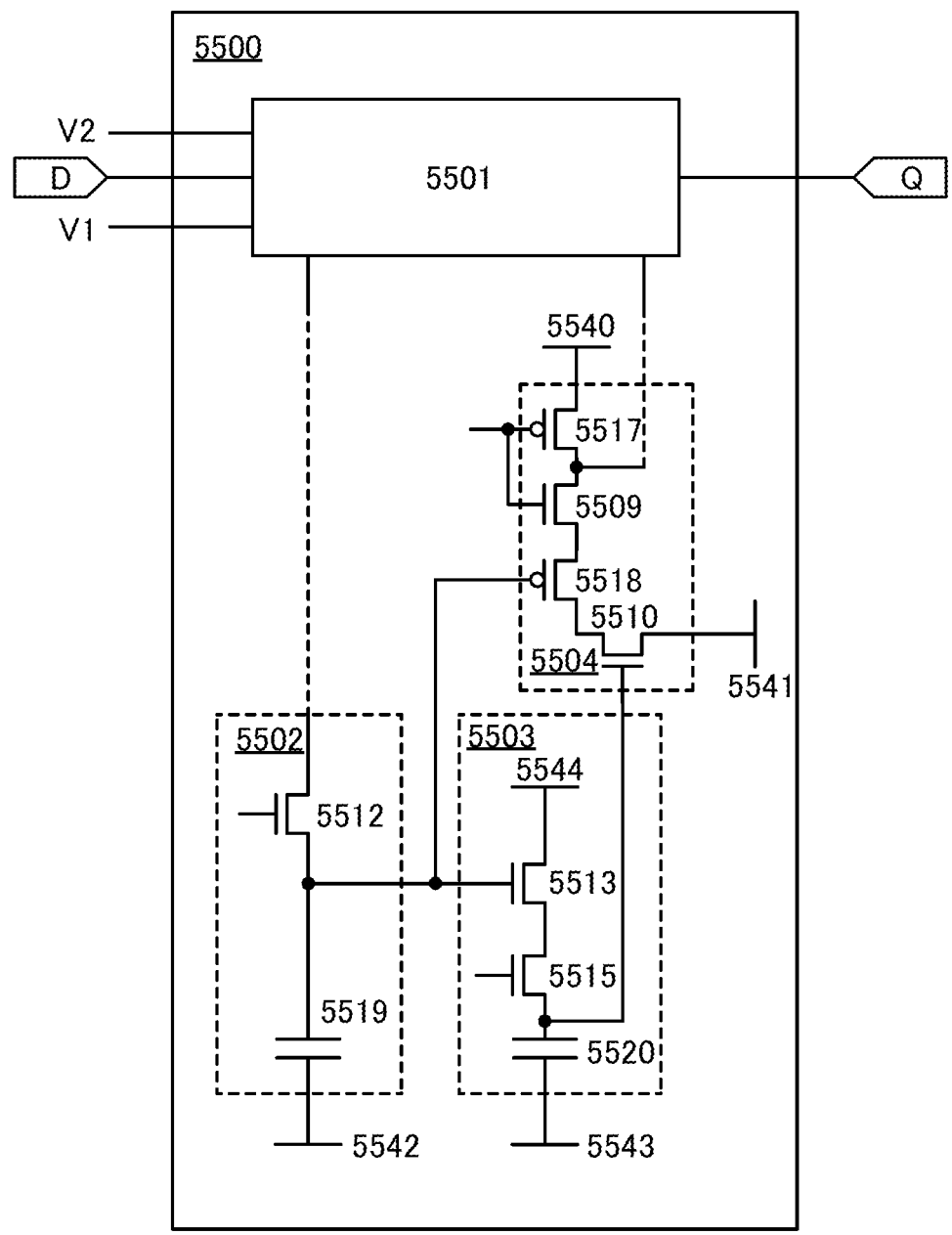
FIG. 11 is a diagram illustrating a structure example of a semiconductor device.

A semiconductor device 5500 shown in FIG. 11 is an example of the flip-flop circuit capable of backup operation. The semiconductor device 5500 includes a first memory circuit 5501, a second memory circuit 5502, a third memory circuit 5503, and a read circuit 5504. As a power supply voltage, a potential difference between a potential V1 and a potential V2 is supplied to the semiconductor device 5500. One of the potential V1 and the potential V2 is at a high level, and the other is at a low level. An example of the structure of the semiconductor device 5500 when the potential V1 is at a low level and the potential V2 is at a high level is described below.

The first memory circuit 5501 has a function of retaining data when a signal D including the data is input in a period during which the power supply voltage is supplied to the semiconductor device 5500. Furthermore, the first memory circuit 5501 outputs a signal Q including the retained data in the period during which the power supply voltage is supplied to the semiconductor device 5500. On the other hand, the first memory circuit 5501 cannot retain data in a period during which the power supply voltage is not supplied to the semiconductor device 5500. That is, the first memory circuit 5501 can be referred to as a volatile memory circuit.

The second memory circuit 5502 has a function of reading the data retained in the first memory circuit 5501 to store (or save) it. The third memory circuit 5503 has a function of reading the data retained in the second memory circuit 5502 to store (or save) it. The read circuit 5504 has a function of reading the data retained in the second memory circuit 5502 or the third memory circuit 5503 to store (or restore) it in the first memory circuit 5501.

In particular, the third memory circuit 5503 has a function of reading the data retained in the second memory circuit 5502 to store (or save) it even in the period during which the power supply voltage is not supplied to the semiconductor device 5500.

As shown in FIG. 11, the second memory circuit 5502 includes a transistor 5512 and a capacitor 5519. The third memory circuit 5503 includes a transistor 5513, a transistor 5515, and a capacitor 5520. The read circuit 5504 includes a transistor 5510, a transistor 5518, a transistor 5509, and a transistor 5517.

The transistor 5512 has a function of charging and discharging the capacitor 5519 in accordance with data retained in the first memory circuit 5501. The transistor 5512 is desirably capable of charging and discharging the capacitor 5519 at a high speed in accordance with data retained in the first memory circuit 5501. Specifically, the transistor 5512 desirably contains crystalline silicon (preferably polycrystalline silicon, further preferably single crystal silicon) in a channel formation region.

The conduction state or the non-conduction state of the transistor 5513 is determined in accordance with the charge retained in the capacitor 5519. The transistor 5515 has a function of charging and discharging the capacitor 5520 in accordance with the potential of a wiring 5544 when the transistor 5513 is in a conduction state. It is desirable that the off-state current of the transistor 5515 be extremely low. Specifically, the transistor 5515 desirably contains an oxide semiconductor (preferably an oxide containing In, Ga, and Zn) in a channel formation region.

Specific connection relations between the elements are described. One of a source and a drain of the transistor 5512 is connected to the first memory circuit 5501. The other of the source and the drain of the transistor 5512 is connected to one electrode of the capacitor 5519, a gate of the transistor 5513, and a gate of the transistor 5518. The other electrode of the capacitor 5519 is connected to a wiring 5542. One of a source and a drain of the transistor 5513 is connected to the wiring 5544. The other of the source and the drain of the transistor 5513 is connected to one of a source and a drain of the transistor 5515. The other of the source and the drain of the transistor 5515 is connected to one electrode of the capacitor 5520 and a gate of the transistor 5510. The other electrode of the capacitor 5520 is connected to a wiring 5543. One of a source and a drain of the transistor 5510 is connected to a wiring 5541. The other of the source and the drain of the transistor 5510 is connected to one of a source and a drain of the transistor 5518. The other of the source and the drain of the transistor 5518 is connected to one of a source and a drain of the transistor 5509. The other of the source and the drain of the transistor 5509 is connected to one of a source and a drain of the transistor 5517 and the first memory circuit 5501. The other of the source and the drain of the transistor 5517 is connected to a wiring 5540. Although a gate of the transistor 5509 is connected to a gate of the transistor 5517 in FIG. 11, the gate of the transistor 5509 is not necessarily connected to the gate of the transistor 5517.

As the transistor 5515, a transistor using an oxide semiconductor can be used. Because of the low off-state current of the transistor 5515, the semiconductor device 5500 can retain data for a long time without power supply. The favorable switching characteristics of the transistor 5515 allow the semiconductor device 5500 to perform high-speed backup and recovery.

At least part of this embodiment can be implemented in combination with the other embodiments described in this specification as appropriate.

Embodiment 5

In this embodiment, a structure example of a semiconductor device that can be used for the display device or the sensor device included in the composite device of one embodiment of the present invention is described. The semiconductor device described below can be particularly used for the control portion included in the display device. The semiconductor device described below can be used not only for the control portion but also for an image capturing portion, a sensor portion or the communication portion included in the sensor device, or the like.

Figure 12:
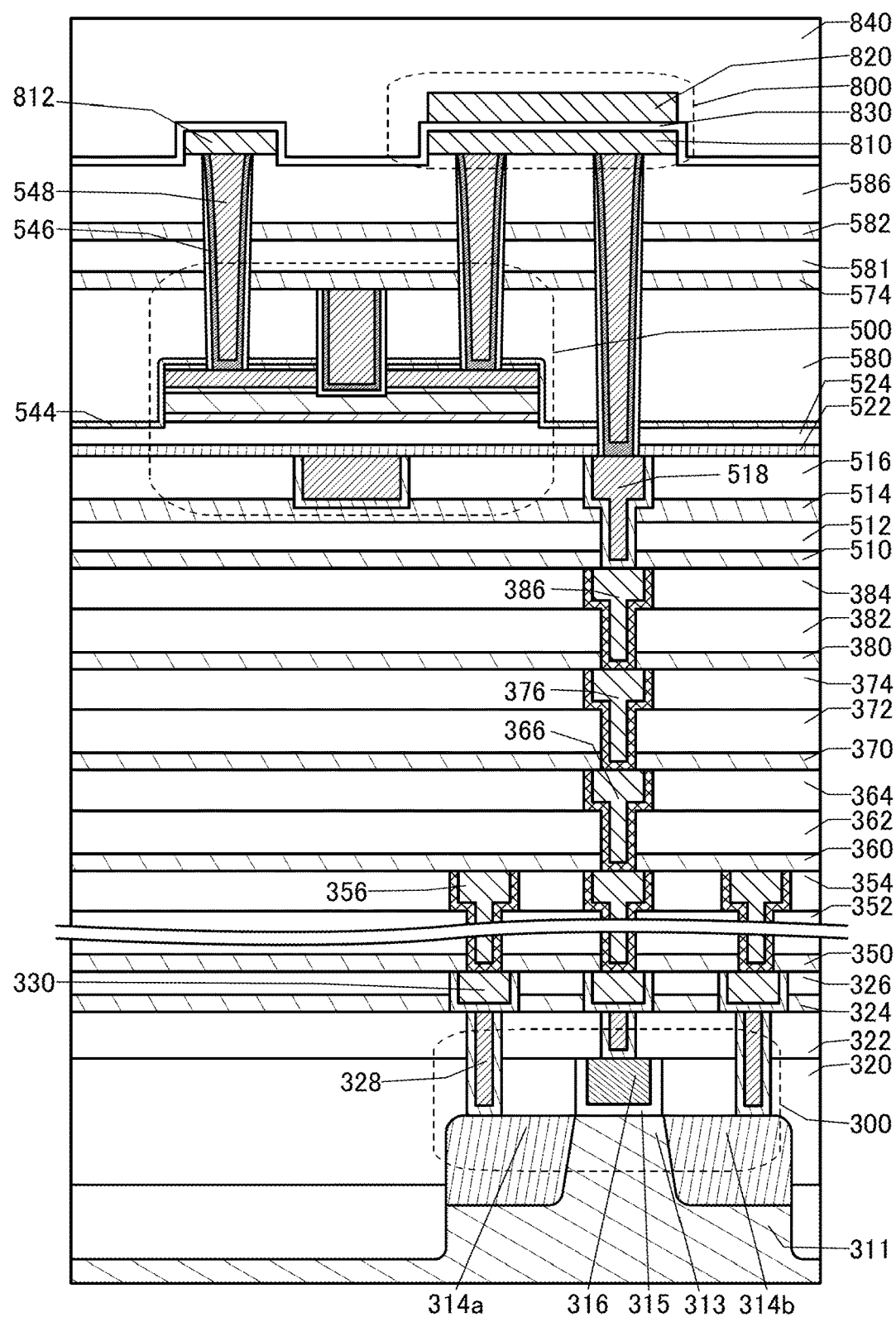
FIG. 12 is a diagram illustrating a structure example of a semiconductor device.
Figure 14A:
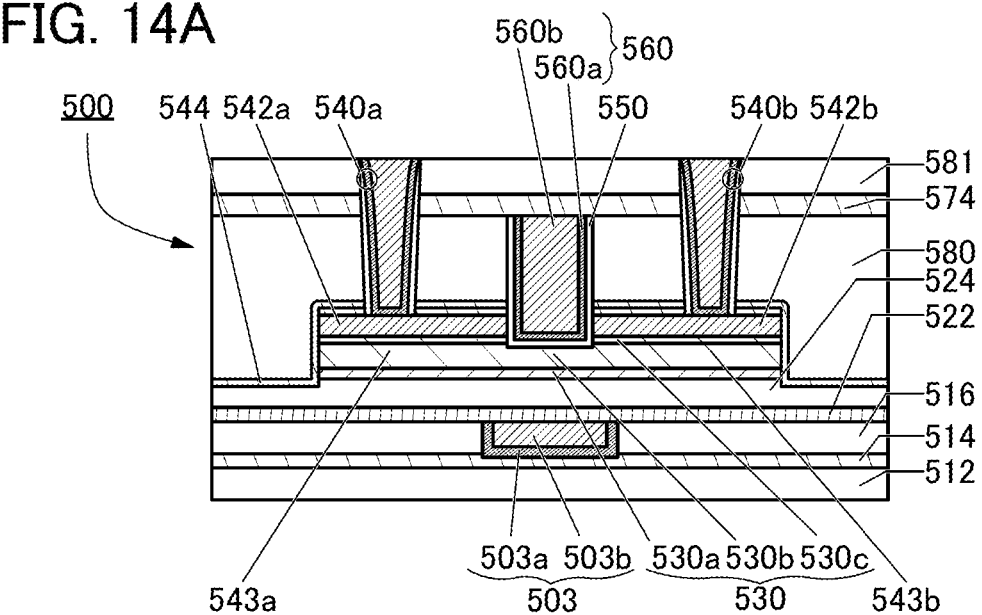
FIG. 14A to FIG. 14C are diagrams illustrating a structure example of a semiconductor device.
Figure 14B:
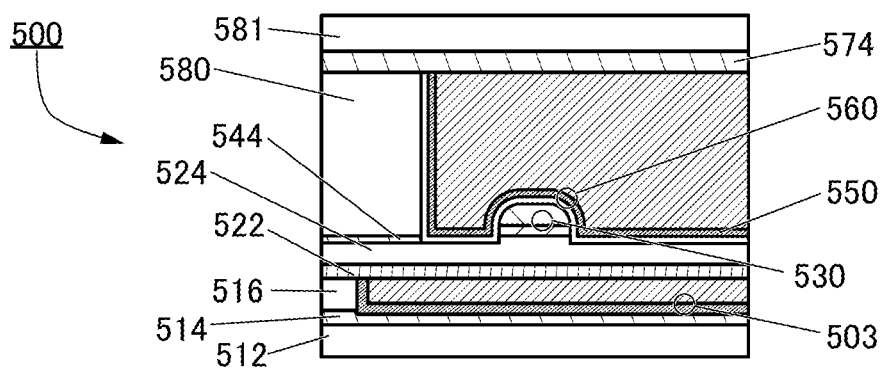
Figure 14C:
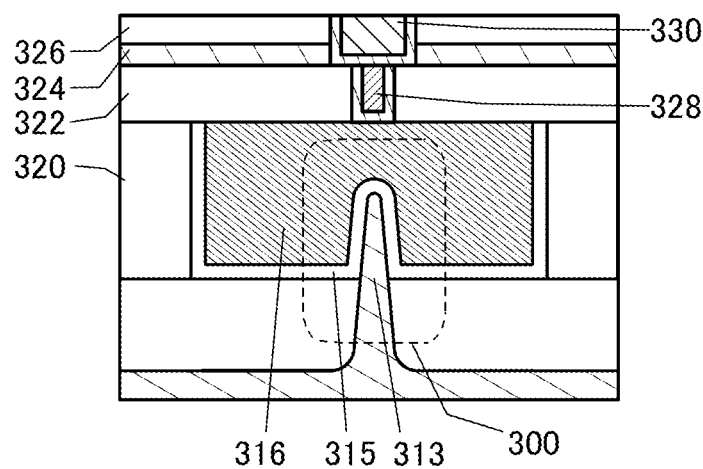

A semiconductor device in FIG. 12 includes a transistor 300, a transistor 500, and a capacitor 800. FIG. 14A is a cross-sectional view of the transistor 500 in the channel length direction, FIG. 14B is a cross-sectional view of the transistor 500 in the channel width direction, and FIG. 14C is a cross-sectional view of the transistor 300 in the channel width direction.

The transistor 500 is a transistor including a metal oxide in its channel formation region (an OS transistor). Since the off-state current of the transistor 500 is low, when the transistor 500 is used as an OS transistor included in the semiconductor device, written data can be retained for a long time.

The semiconductor device described in this embodiment includes the transistor 300, the transistor 500, and the capacitor 800, as shown in FIG. 12. The transistor 500 is provided above the transistor 300, and the capacitor 800 is provided above the transistor 300 and the transistor 500.

The transistor 300 is provided over a substrate 311 and includes a conductor 316, an insulator 315, a semiconductor region 313 that is part of the substrate 311, and a low-resistance region 314*a* and a low-resistance region 314*b* each functioning as a source region or a drain region. Note that the transistor 300 can be used as the transistor included in the memory, for example.

As shown in FIG. 14C, in the transistor 300, a top surface and a side surface in the channel width direction of the semiconductor region 313 are covered with the conductor 316 with the insulator 315 therebetween. Such a Fin-type transistor 300 can have an increased effective channel width, and thus have improved on-state characteristics. In addition, since contribution of an electric field of a gate electrode can be increased, the off-state characteristics of the transistor 300 can be improved.

Note that the transistor 300 can be either a p-channel transistor or an n-channel transistor.

A region of the semiconductor region 313 where a channel is formed, a region in the vicinity thereof, the low-resistance region 314*a* and the low-resistance region 314*b* each functioning as a source region or a drain region, and the like preferably contain a semiconductor such as a silicon-based semiconductor, and preferably contain single crystal silicon. Alternatively, the regions may be formed using a material containing Ge (germanium), SiGe (silicon germanium), GaAs (gallium arsenide), GaAlAs (gallium aluminum arsenide), or the like. A structure may be used in which silicon whose effective mass is controlled by applying stress to the crystal lattice and changing the lattice spacing is used. Alternatively, the transistor 300 may be an HEMT (High Electron Mobility Transistor) with the use of GaAs and GaAlAs, or the like.

The low-resistance region 314*a* and the low-resistance region 314*b* contain an element which imparts n-type conductivity, such as arsenic or phosphorus, or an element which imparts p-type conductivity, such as boron, in addition to the semiconductor material used for the semiconductor region 313.

For the conductor 316 functioning as a gate electrode, a semiconductor material such as silicon containing the element which imparts n-type conductivity, such as arsenic or phosphorus, or the element which imparts p-type conductivity, such as boron, or a conductive material such as a metal material, an alloy material, or a metal oxide material can be used.

Note that since the work function of a conductor depends on the material of the conductor, the threshold voltage of the transistor can be adjusted by selecting the material of the conductor. Specifically, it is preferable to use a material such as titanium nitride or tantalum nitride for the conductor. Moreover, in order to ensure both conductivity and embeddability, it is preferable to use stacked layers of metal materials such as tungsten and aluminum for the conductor, and it is particularly preferable to use tungsten in terms of heat resistance.

Figure 13:
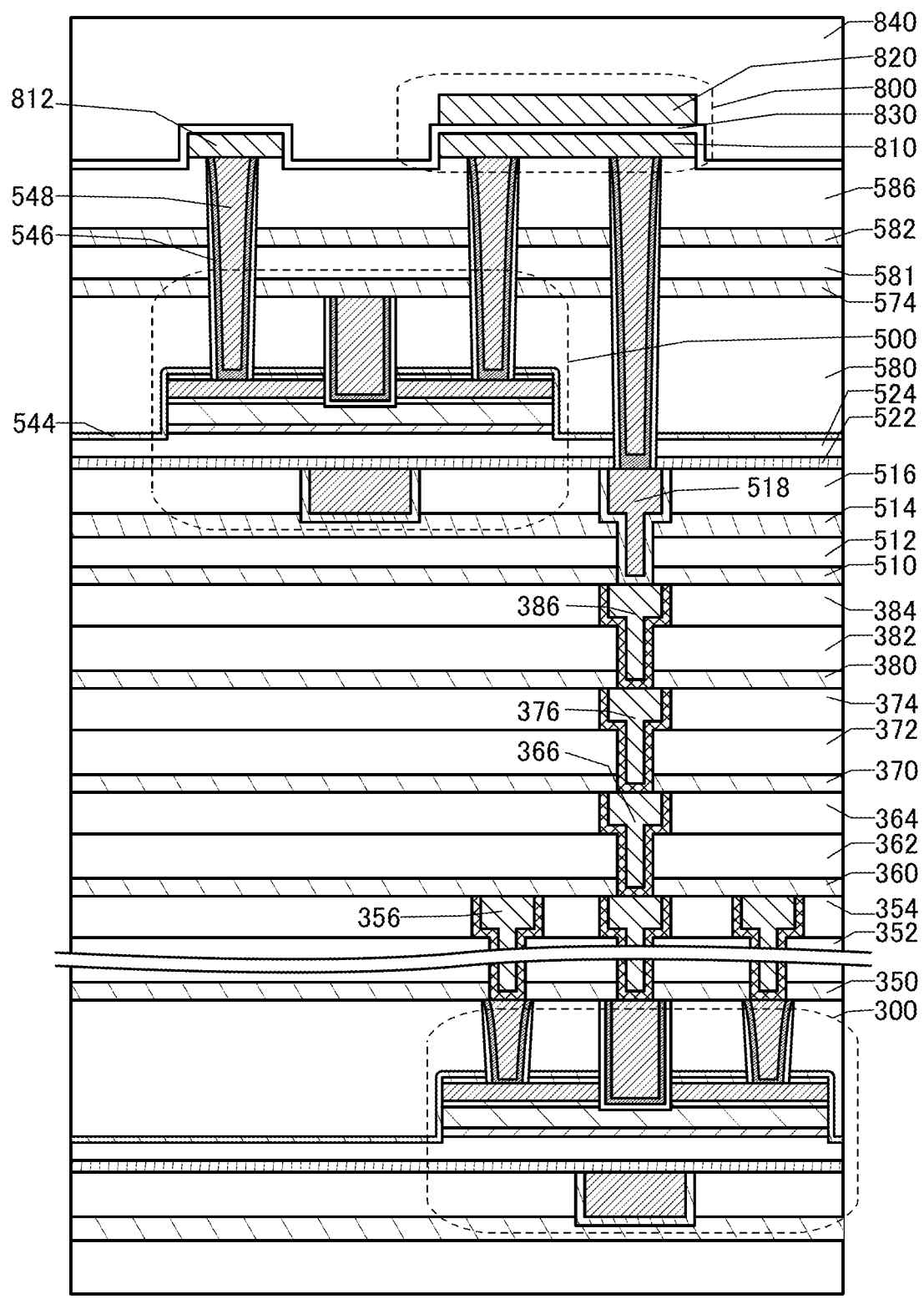
FIG. 13 is a diagram illustrating a structure example of a semiconductor device.

Note that the transistor 300 shown in FIG. 12 is an example and the structure is not limited thereto; an appropriate transistor is used in accordance with a circuit structure or a driving method. For example, when the semiconductor device is composed of only OS transistors, the transistor 300 has a structure similar to that of the transistor 500 using an oxide semiconductor, as shown in FIG. 13. Note that the details of the transistor 500 are described later.

An insulator 320, an insulator 322, an insulator 324, and an insulator 326 are stacked sequentially and provided to cover the transistor 300.

For the insulator 320, the insulator 322, the insulator 324, and the insulator 326, silicon oxide, silicon oxynitride, silicon nitride oxide, silicon nitride, aluminum oxide, aluminum oxynitride, aluminum nitride oxide, aluminum nitride, or the like is used, for example.

Note that in this specification, silicon oxynitride refers to a material that contains oxygen at a higher proportion than nitrogen, and silicon nitride oxide refers to a material that contains nitrogen at a higher proportion than oxygen. Furthermore, in this specification, aluminum oxynitride refers to a material that contains oxygen at a higher proportion than nitrogen, and aluminum nitride oxide refers to a material that contains nitrogen at a higher proportion than oxygen.

The insulator 322 may have a function of a planarization film for planarizing a level difference caused by the transistor 300 or the like provided below the insulator 322. For example, a top surface of the insulator 322 may be planarized by planarization treatment using a chemical mechanical polishing (CMP) method or the like to improve planarity.

In addition, for the insulator 324, it is preferable to use a film having a barrier property that prevents diffusion of hydrogen or impurities from the substrate 311, the transistor 300, or the like into a region where the transistor 500 is provided.

For the film having a barrier property against hydrogen, silicon nitride formed by a CVD method can be used, for example. Here, diffusion of hydrogen to a semiconductor element including an oxide semiconductor, such as the transistor 500, degrades the characteristics of the semiconductor element in some cases. Therefore, a film that inhibits hydrogen diffusion is preferably used between the transistor 500 and the transistor 300. The film that inhibits hydrogen diffusion is specifically a film from which a small amount of hydrogen is released.

The amount of released hydrogen can be analyzed by thermal desorption spectroscopy (TDS) or the like, for example. The amount of hydrogen released from the insulator 324 that is converted into hydrogen atoms per area of the insulator 324 is less than or equal to $10 \times 10^{15}$ atoms/cm$^2$, preferably less than or equal to $5 \times 10^{15}$ atoms/cm$^2$, in the TDS analysis in a film-surface temperature range of 50° C. to 500° C., for example.

Note that the dielectric constant of the insulator 326 is preferably lower than that of the insulator 324. For example, the dielectric constant of the insulator 326 is preferably lower than 4, further preferably lower than 3. The dielectric constant of the insulator 326 is, for example, preferably 0.7 times or less, further preferably 0.6 times or less the dielectric constant of the insulator 324. When a material with a low dielectric constant is used as an interlayer film, the parasitic capacitance generated between wirings can be reduced.

In addition, a conductor 328, a conductor 330, and the like that are connected to the capacitor 800 or the transistor 500 are embedded in the insulator 320, the insulator 322, the insulator 324, and the insulator 326. Note that the conductor 328 and the conductor 330 each have a function of a plug or a wiring. Furthermore, a plurality of conductors functioning as plugs or wirings are collectively denoted by the same reference numeral in some cases. Moreover, in this specification and the like, a wiring and a plug connected to the wiring may be a single component. That is, there are cases where part of a conductor functions as a wiring and part of a conductor functions as a plug.

As a material for each of the plugs and wirings (the conductor 328, the conductor 330, and the like), a single layer or a stacked layer of a conductive material such as a metal material, an alloy material, a metal nitride material, or a metal oxide material can be used. It is preferable to use a high-melting-point material that has both heat resistance and conductivity, such as tungsten or molybdenum, and it is preferable to use tungsten. Alternatively, it is preferable to form the plugs and wirings with a low-resistance conductive material such as aluminum or copper. The use of a low-resistance conductive material can reduce wiring resistance.

A wiring layer may be provided over the insulator 326 and the conductor 330. For example, in FIG. 12, an insulator 350, an insulator 352, and an insulator 354 are stacked sequentially and provided. Furthermore, a conductor 356 is formed in the insulator 350, the insulator 352, and the insulator 354. The conductor 356 has a function of a plug or a wiring that is connected to the transistor 300. Note that the conductor 356 can be provided using a material similar to those for the conductor 328 and the conductor 330.

Note that for example, as the insulator 350, like the insulator 324, an insulator having a barrier property against hydrogen is preferably used. Furthermore, the conductor 356 preferably contains a conductor having a barrier property against hydrogen. In particular, the conductor having a barrier property against hydrogen is formed in an opening of the insulator 350 having a barrier property against hydrogen. With this structure, the transistor 300 and the transistor 500 can be separated by a barrier layer, so that diffusion of hydrogen from the transistor 300 into the transistor 500 can be inhibited.

Note that for the conductor having a barrier property against hydrogen, tantalum nitride is preferably used, for example. In addition, the use of a stack including tantalum nitride and tungsten, which has high conductivity, can inhibit diffusion of hydrogen from the transistor 300 while the conductivity of a wiring is kept. In that case, a structure is preferable in which a tantalum nitride layer having a barrier property against hydrogen is in contact with the insulator 350 having a barrier property against hydrogen.

A wiring layer may be provided over the insulator 354 and the conductor 356. For example, in FIG. 12, an insulator 360, an insulator 362, and an insulator 364 are stacked sequentially and provided. Furthermore, a conductor 366 is formed in the insulator 360, the insulator 362, and the insulator 364. The conductor 366 has a function of a plug or a wiring. Note that the conductor 366 can be provided using a material similar to those for the conductor 328 and the conductor 330.

Note that for example, as the insulator 360, like the insulator 324, an insulator having a barrier property against hydrogen is preferably used. Furthermore, the conductor 366 preferably contains a conductor having a barrier property against hydrogen. In particular, the conductor having a barrier property against hydrogen is formed in an opening portion of the insulator 360 having a barrier property against hydrogen. With this structure, the transistor 300 and the transistor 500 can be separated by a barrier layer, so that diffusion of hydrogen from the transistor 300 into the transistor 500 can be inhibited.

A wiring layer may be provided over the insulator 364 and the conductor 366. For example, in FIG. 12, an insulator 370, an insulator 372, and an insulator 374 are stacked sequentially and provided. Furthermore, a conductor 376 is formed in the insulator 370, the insulator 372, and the insulator 374. The conductor 376 has a function of a plug or a wiring. Note that the conductor 376 can be provided using a material similar to those for the conductor 328 and the conductor 330.

Note that for example, as the insulator 370, like the insulator 324, an insulator having a barrier property against hydrogen is preferably used. Furthermore, the conductor 376 preferably contains a conductor having a barrier property against hydrogen. In particular, the conductor having a barrier property against hydrogen is formed in an opening portion of the insulator 370 having a barrier property against hydrogen. With this structure, the transistor 300 and the transistor 500 can be separated by a barrier layer, so that diffusion of hydrogen from the transistor 300 into the transistor 500 can be inhibited.

A wiring layer may be provided over the insulator 374 and the conductor 376. For example, in FIG. 12, an insulator 380, an insulator 382, and an insulator 384 are stacked sequentially and provided. Furthermore, a conductor 386 is formed in the insulator 380, the insulator 382, and the insulator 384. The conductor 386 has a function of a plug or a wiring. Note that the conductor 386 can be provided using a material similar to those for the conductor 328 and the conductor 330.

Note that for example, as the insulator 380, like the insulator 324, an insulator having a barrier property against hydrogen is preferably used. Furthermore, the conductor 386 preferably contains a conductor having a barrier property against hydrogen. In particular, the conductor having a barrier property against hydrogen is formed in an opening portion of the insulator 380 having a barrier property against hydrogen. With this structure, the transistor 300 and the transistor 500 can be separated by a barrier layer, so that diffusion of hydrogen from the transistor 300 into the transistor 500 can be inhibited.

Although the wiring layer including the conductor 356, the wiring layer including the conductor 366, the wiring layer including the conductor 376, and the wiring layer including the conductor 386 are described above, the semiconductor device of this embodiment is not limited thereto. Three or less wiring layers that are similar to the wiring layer including the conductor 356 may be provided, or five or more wiring layers that are similar to the wiring layer including the conductor 356 may be provided.

An insulator 510, an insulator 512, an insulator 514, and an insulator 516 are stacked sequentially and provided over the insulator 384. A substance having a barrier property against oxygen or hydrogen is preferably used for any of the insulator 510, the insulator 512, the insulator 514, and the insulator 516.

For example, for the insulator 510 and the insulator 514, it is preferable to use a film having a barrier property that prevents diffusion of hydrogen or impurities from the substrate 311, a region where the transistor 300 is provided, or the like into the region where the transistor 500 is provided. Therefore, a material similar to that for the insulator 324 can be used.

For the film having a barrier property against hydrogen, silicon nitride formed by a CVD method can be used, for example. Here, diffusion of hydrogen to a semiconductor element including an oxide semiconductor, such as the transistor 500, degrades the characteristics of the semiconductor element in some cases. Therefore, a film that inhibits hydrogen diffusion is preferably used between the transistor 500 and the transistor 300. The film that inhibits hydrogen diffusion is specifically a film from which a small amount of hydrogen is released.

In addition, for the film having a barrier property against hydrogen, a metal oxide such as aluminum oxide, hafnium oxide, or tantalum oxide is preferably used for the insulator 510 and the insulator 514, for example.

In particular, aluminum oxide has an excellent blocking effect that prevents the passage of both oxygen and impurities such as hydrogen and moisture, which are factors of a change in electrical characteristics of the transistor. Accordingly, aluminum oxide can prevent mixing of impurities such as hydrogen and moisture into the transistor 500 in a manufacturing process and after manufacturing of the transistor. In addition, release of oxygen from the oxide included in the transistor 500 can be inhibited. Therefore, aluminum oxide is suitably used for a protective film of the transistor 500.

In addition, for the insulator 512 and the insulator 516, a material similar to that for the insulator 320 can be used, for example. Furthermore, when a material with a comparatively low dielectric constant is used for these insulators, parasitic capacitance generated between wirings can be reduced. A silicon oxide film, a silicon oxynitride film, or the like can be used for the insulator 512 and the insulator 516, for example.

Furthermore, a conductor 518, a conductor included in the transistor 500 (a conductor 503 for example), and the like are embedded in the insulator 510, the insulator 512, the insulator 514, and the insulator 516. Note that the conductor 518 has a function of a plug or a wiring that is connected to the capacitor 800 or the transistor 300. The conductor 518 can be provided using a material similar to those for the conductor 328 and the conductor 330.

In particular, the conductor 518 in a region in contact with the insulator 510 and the insulator 514 is preferably a conductor having a barrier property against oxygen, hydrogen, and water. With this structure, the transistor 300 and the transistor 500 can be separated by a layer having a barrier property against oxygen, hydrogen, and water; thus, diffusion of hydrogen from the transistor 300 into the transistor 500 can be inhibited.

The transistor 500 is provided above the insulator 516.

As shown in FIG. 14A and FIG. 14B, the transistor 500 includes the conductor 503 positioned to be embedded in the insulator 514 and the insulator 516; an insulator 522 positioned over the insulator 516 and the conductor 503; an insulator 524 positioned over the insulator 522; an oxide 530a positioned over the insulator 524; an oxide 530b positioned over the oxide 530a; an oxide 530c positioned over the oxide 530b; a conductor 542a and a conductor 542b positioned apart from each other over the oxide 530c; an insulator 580 that is positioned over the conductor 542a and the conductor 542b and is provided with an opening formed to overlap with a region between the conductor 542a and the conductor 542b; an insulator 550 positioned on a bottom and a side surface of the opening; and a conductor 560 positioned on a formation surface of the insulator 550.

In addition, as shown in FIG. 14A and FIG. 14B, an insulator 544 is preferably positioned between the insulator 580 and the oxide 530a, the oxide 530b, the conductor 542a, and the conductor 542b. Furthermore, as shown in FIG. 14A and FIG. 14B, the conductor 560 preferably includes a conductor 560a provided inside the insulator 550 and a conductor 560b provided to be embedded inside the conductor 560a. Moreover, as shown in FIG. 14A and FIG. 14B, an insulator 574 is preferably positioned over the insulator 580, the conductor 560, and the insulator 550.

Note that in the following description, the oxide 530a, the oxide 530b, and the oxide 530c are sometimes collectively referred to as an oxide 530.

Note that although a structure of the transistor 500 in which three layers of the oxide 530a, the oxide 530b, and the oxide 530c are stacked in a region where a channel is formed and its vicinity is shown, the present invention is not limited thereto. For example, a single layer of the oxide 530b, a two-layer structure of the oxide 530b and the oxide 530a, a two-layer structure of the oxide 530b and the oxide 530c, or a stacked-layer structure of four or more layers may be employed. Furthermore, although the conductor 560 is shown to have a stacked-layer structure of two layers in the transistor 500, the present invention is not limited thereto. For example, the conductor 560 may have a single-layer structure or a stacked-layer structure of three or more layers. Moreover, the transistor 500 shown in FIG. 12 and FIG. 14A is an example and the structure is not limited thereto; an appropriate transistor is used in accordance with a circuit configuration or a driving method.

Here, the conductor 560 functions as a gate electrode of the transistor, and the conductor 542a and the conductor

542b each function as a source electrode or a drain electrode. As described above, the conductor 560 is formed to be embedded in the opening of the insulator 580 and the region between the conductor 542a and the conductor 542b. The positions of the conductor 560, the conductor 542a, and the conductor 542b with respect to the opening of the insulator 580 are selected in a self-aligned manner. That is, in the transistor 500, the gate electrode can be positioned between the source electrode and the drain electrode in a self-aligned manner. Therefore, the conductor 560 can be formed without an alignment margin, resulting in a reduction in the area occupied by the transistor 500. Accordingly, miniaturization and high integration of the semiconductor device can be achieved.

In addition, since the conductor 560 is formed in the region between the conductor 542a and the conductor 542b in a self-aligned manner, the conductor 560 does not have a region overlapping with the conductor 542a or the conductor 542b. Thus, parasitic capacitance formed between the conductor 560 and each of the conductor 542a and the conductor 542b can be reduced. As a result, the switching speed of the transistor 500 can be improved, and the transistor 500 can have high frequency characteristics.

The conductor 560 sometimes functions as a first gate (also referred to as top gate) electrode. In addition, the conductor 503 sometimes functions as a second gate (also referred to as bottom gate) electrode. In that case, the threshold voltage of the transistor 500 can be controlled by changing a potential applied to the conductor 503 independently of a potential applied to the conductor 560. In particular, the threshold voltage of the transistor 500 can be higher than 0 V and the off-state current can be reduced by applying a negative potential to the conductor 503. Thus, a drain current at the time when a potential applied to the conductor 560 is 0 V can be lower in the case where a negative potential is applied to the conductor 503 than in the case where a negative potential is not applied to the conductor 503.

The conductor 503 is positioned to overlap with the oxide 530 and the conductor 560. Thus, in the case where potentials are applied to the conductor 560 and the conductor 503, an electric field generated from the conductor 560 and an electric field generated from the conductor 503 are connected, so that a channel formation region formed in the oxide 530 can be covered. In this specification and the like, a transistor structure in which a channel formation region is electrically surrounded by electric fields of a first gate electrode and a second gate electrode is referred to as a surrounded channel (S-channel) structure.

In addition, the conductor 503 has a structure similar to that of the conductor 518; a conductor 503a is formed in contact with an inner wall of an opening in the insulator 514 and the insulator 516, and a conductor 503b is formed on the inner side. Note that although the transistor 500 having a structure in which the conductor 503a and the conductor 503b are stacked is shown, the present invention is not limited thereto. For example, the conductor 503 may be provided as a single layer or to have a stacked-layer structure of three or more layers.

Here, for the conductor 503a, a conductive material that has a function of inhibiting diffusion of impurities such as a hydrogen atom, a hydrogen molecule, a water molecule, and a copper atom (through which the impurities are less likely to pass) is preferably used. Alternatively, it is preferable to use a conductive material that has a function of inhibiting diffusion of oxygen (e.g., at least one of an oxygen atom, an oxygen molecule, and the like) (through which oxygen is less likely to pass). Note that in this specification, a function of inhibiting diffusion of impurities or oxygen means a function of inhibiting diffusion of any one or all of the impurities and oxygen.

For example, when the conductor 503a has a function of inhibiting diffusion of oxygen, a reduction in conductivity of the conductor 503b due to oxidation can be inhibited.

In addition, in the case where the conductor 503 also functions as a wiring, a conductive material with high conductivity that contains tungsten, copper, or aluminum as its main component is preferably used for the conductor 503b. Note that the conductor 503b is shown as a single layer but may have a stacked-layer structure, for example, a stack of the above conductive material and titanium or titanium nitride.

The insulator 522, the insulator 524, and the insulator 550 have a function of a gate insulating film.

Here, as the insulator 524 and the insulator 550 that are in contact with the oxide 530, an insulator that contains oxygen more than oxygen in the stoichiometric composition is preferably used. That is, an excess-oxygen region is preferably formed in the insulator 524 and the insulator 550. When such an insulator containing excess oxygen is provided in contact with the oxide 530, oxygen vacancies in the oxide 530 can be reduced and the reliability of the transistor 500 can be improved.

As the insulator including an excess-oxygen region, specifically, an oxide material that releases part of oxygen by heating is preferably used. An oxide that releases oxygen by heating is an oxide film in which the amount of released oxygen converted into oxygen atoms is greater than or equal to $1.0 \times 10^{18}$ atoms/cm$^3$, preferably greater than or equal to $1.0 \times 10^{19}$ atoms/cm$^3$, further preferably greater than or equal to $2.0 \times 10^{19}$ atoms/cm$^3$ or greater than or equal to $3.0 \times 10^{20}$ atoms/cm$^3$ in TDS (Thermal Desorption Spectroscopy) analysis. Note that the temperature of the film surface in the TDS analysis is preferably in a range of higher than or equal to 100° C. and lower than or equal to 700° C., or higher than or equal to 100° C. and lower than or equal to 400° C.

In addition, in the case where the insulator 524 includes an excess-oxygen region, it is preferable that the insulator 522 have a function of inhibiting diffusion of oxygen (e.g., an oxygen atom, an oxygen molecule, or the like) (through which oxygen is less likely to pass).

When the insulator 522 has a function of inhibiting diffusion of oxygen or impurities, oxygen contained in the oxide 530 is not diffused into the insulator 516 side, which is preferable. Furthermore, the conductor 503 can be inhibited from reacting with oxygen contained in the insulator 524 or the oxide 530.

For the insulator 522, a single layer or stacked layers of an insulator containing what is called a high-k material such as aluminum oxide, hafnium oxide, an oxide containing aluminum and hafnium (hafnium aluminate), tantalum oxide, zirconium oxide, lead zirconate titanate (PZT), strontium titanate (SrTiO$_3$), or (Ba,Sr)TiO$_3$ (BST) are preferably used, for example. As miniaturization and high integration of transistors progress, a problem such as leakage current might arise because of a thinner gate insulating film. When a high-k material is used for an insulator functioning as the gate insulating film, a gate potential during transistor operation can be reduced while the physical thickness is maintained.

It is particularly preferable to use an insulator containing an oxide of one or both of aluminum and hafnium, which is/are an insulating material having a function of inhibiting diffusion of impurities, oxygen, and the like (through which oxygen is less likely to pass). Aluminum oxide, hafnium oxide, an oxide containing aluminum and hafnium (hafnium aluminate), or the like is preferably used as the insulator containing an oxide of one or both of aluminum and hafnium. In the case where the insulator 522 is formed using such a material, the insulator 522 functions as a layer that inhibits release of oxygen from the oxide 530 and mixing of impurities such as hydrogen from the periphery of the transistor 500 into the oxide 530.

Alternatively, aluminum oxide, bismuth oxide, germanium oxide, niobium oxide, silicon oxide, titanium oxide, tungsten oxide, yttrium oxide, or zirconium oxide may be added to these insulators, for example. Alternatively, these insulators may be subjected to nitriding treatment. The insulator over which silicon oxide, silicon oxynitride, or silicon nitride is stacked may be used.

Note that in the transistor 500 in FIG. 14A and FIG. 14B, the insulator 522 and the insulator 524 are shown as the second gate insulating film having a stacked-layer structure of two layers; however, the second gate insulating film may be a single layer or may have a stacked-layer structure of three or more layers. In such cases, without limitation to a stacked-layer structure formed of the same material, a stacked-layer structure formed of different materials may be employed.

In the transistor 500, a metal oxide functioning as an oxide semiconductor is preferably used as the oxide 530 including the channel formation region. For example, as the oxide 530, a metal oxide such as an In-M-Zn oxide (the element M is one kind or a plurality of kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like) is preferably used. The In-M-Zn oxide that can be used as the oxide 530 is particularly preferably a CAAC-OS or a CAC-OS described later. Furthermore, as the oxide 530, an In—Ga oxide or an In—Zn oxide may be used.

The metal oxide functioning as the channel formation region in the oxide 530 has a band gap of more than or equal to 2 eV, preferably more than or equal to 2.5 eV. With the use of a metal oxide having such a wide bandgap, the off-state current of the transistor can be reduced.

When the oxide 530 includes the oxide 530a under the oxide 530b, it is possible to inhibit diffusion of impurities into the oxide 530b from the components formed below the oxide 530a. Moreover, including the oxide 530c over the oxide 530b makes it possible to inhibit diffusion of impurities into the oxide 530b from the components formed above the oxide 530c.

Note that the oxide 530 preferably has a stacked-layer structure of a plurality of oxide layers that differ in the atomic ratio of metal atoms. Specifically, the atomic ratio of the element M to the constituent elements in the metal oxide used as the oxide 530a is preferably higher than the atomic ratio of the element M to the constituent elements in the metal oxide used as the oxide 530b. In addition, the atomic ratio of the element M to In in the metal oxide used as the oxide 530a is preferably higher than the atomic ratio of the element M to In in the metal oxide used as the oxide 530b. Furthermore, the atomic ratio of In to the element M in the metal oxide used as the oxide 530b is preferably higher than the atomic ratio of In to the element M in the metal oxide used as the oxide 530a. Moreover, a metal oxide that can be used as the oxide 530a or the oxide 530b can be used as the oxide 530c.

In addition, the energy of the conduction band minimum of each of the oxide 530a and the oxide 530c is preferably higher than the energy of the conduction band minimum of the oxide 530b. In other words, the electron affinity of each of the oxide 530a and the oxide 530c is preferably smaller than the electron affinity of the oxide 530b.

Here, the energy level of the conduction band minimum gradually changes at junction portions of the oxide 530a, the oxide 530b, and the oxide 530c. In other words, the energy level of the conduction band minimum at the junction portions of the oxide 530a, the oxide 530b, and the oxide 530c continuously changes or is continuously connected. To change the energy level gradually, the densities of defect states in mixed layers formed at an interface between the oxide 530a and the oxide 530b and an interface between the oxide 530b and the oxide 530c is preferably made low.

Specifically, when the oxide 530a and the oxide 530b or the oxide 530b and the oxide 530c contain a common element (as a main component) in addition to oxygen, a mixed layer with a low density of defect states can be formed. For example, in the case where the oxide 530b is an In—Ga—Zn oxide, an In—Ga—Zn oxide, a Ga—Zn oxide, gallium oxide, or the like is preferably used as the oxide 530a and the oxide 530c.

At this time, the oxide 530b serves as a main carrier path. When the oxide 530a and the oxide 530c have the above structures, the densities of defect states at the interface between the oxide 530a and the oxide 530b and the interface between the oxide 530b and the oxide 530c can be made low. Thus, the influence of interface scattering on carrier conduction is small, and the transistor 500 can have a high on-state current.

The conductor 542a and the conductor 542b functioning as the source electrode and the drain electrode are provided over the oxide 530c. For the conductor 542a and conductor 542b, it is preferable to use a metal element selected from aluminum, chromium, copper, silver, gold, platinum, tantalum, nickel, titanium, molybdenum, tungsten, hafnium, vanadium, niobium, manganese, magnesium, zirconium, beryllium, indium, ruthenium, iridium, strontium, and lanthanum; an alloy containing the above metal element; an alloy containing a combination of the above metal element; or the like. For example, it is preferable to use tantalum nitride, titanium nitride, tungsten, a nitride containing titanium and aluminum, a nitride containing tantalum and aluminum, ruthenium oxide, ruthenium nitride, an oxide containing strontium and ruthenium, an oxide containing lanthanum and nickel, or the like. In addition, tantalum nitride, titanium nitride, a nitride containing titanium and aluminum, a nitride containing tantalum and aluminum, ruthenium oxide, ruthenium nitride, an oxide containing strontium and ruthenium, and an oxide containing lanthanum and nickel are preferable because they are oxidation-resistant conductive materials or materials that retain their conductivity even after absorbing oxygen. Furthermore, a metal nitride film of tantalum nitride or the like is preferable because it has a barrier property against hydrogen or oxygen.

In addition, although the conductor 542a and the conductor 542b each having a single-layer structure are shown in FIG. 14A and FIG. 14B, a stacked-layer structure of two or more layers may be employed. For example, it is preferable to stack a tantalum nitride film and a tungsten film. Alternatively, a titanium film and an aluminum film may be stacked. Alternatively, a two-layer structure where an aluminum film is stacked over a tungsten film, a two-layer structure where a copper film is stacked over a copper-magnesium-aluminum alloy film, a two-layer structure where a copper film is stacked over a titanium film, or a two-layer structure where a copper film is stacked over a tungsten film may be employed.

Other examples include a three-layer structure where a titanium film or a titanium nitride film is formed, an aluminum film or a copper film is stacked over the titanium film or the titanium nitride film, and a titanium film or a titanium nitride film is formed over the aluminum film or the copper film; and a three-layer structure where a molybdenum film or a molybdenum nitride film is formed, an aluminum film or a copper film is stacked over the molybdenum film or the molybdenum nitride film, and a molybdenum film or a molybdenum nitride film is formed over the aluminum film or the copper film. Note that a transparent conductive material containing indium oxide, tin oxide, or zinc oxide may be used.

In addition, as shown in FIG. 14A, a region 543a and a region 543b are sometimes formed as low-resistance regions at an interface between the oxide 530 and the conductor 542a (the conductor 542b) and in the vicinity of the interface. In that case, the region 543a functions as one of a source region and a drain region, and the region 543b functions as the other of the source region and the drain region. Furthermore, the channel formation region is formed in a region between the region 543a and the region 543b.

When the conductor 542a (the conductor 542b) is provided to be in contact with the oxide 530, the oxygen concentration in the region 543a (the region 543b) sometimes decreases. In addition, a metal compound layer that contains the metal contained in the conductor 542a (the conductor 542b) and the component of the oxide 530 is sometimes formed in the region 543a (the region 543b). In such a case, the carrier density of the region 543a (the region 543b) increases, and the region 543a (the region 543b) becomes a low-resistance region.

The insulator 544 is provided to cover the conductor 542a and the conductor 542b and inhibits oxidation of the conductor 542a and the conductor 542b. At this time, the insulator 544 may be provided to cover a side surface of the oxide 530 and to be in contact with the insulator 524.

A metal oxide containing one kind or two or more kinds selected from hafnium, aluminum, gallium, yttrium, zirconium, tungsten, titanium, tantalum, nickel, germanium, neodymium, lanthanum, magnesium, and the like can be used as the insulator 544. Alternatively, silicon nitride oxide, silicon nitride, or the like can be used as the insulator 544.

It is particularly preferable to use an insulator containing an oxide of one or both of aluminum and hafnium, such as aluminum oxide, hafnium oxide, or an oxide containing aluminum and hafnium (hafnium aluminate), as the insulator 544. In particular, hafnium aluminate has higher heat resistance than a hafnium oxide film. Therefore, hafnium aluminate is preferable because it is less likely to be crystallized by heat treatment in a later step. Note that the insulator 544 is not an essential component when the conductor 542a and the conductor 542b are oxidation-resistant materials or do not significantly lose their conductivity even after absorbing oxygen. Design is appropriately set in consideration of required transistor characteristics.

When the insulator 544 is included, diffusion of impurities such as water and hydrogen contained in the insulator 580 into the oxide 530b through the oxide 530c and the insulator 550 can be inhibited. Furthermore, oxidation of the conductor 560 due to excess oxygen contained in the insulator 580 can be inhibited.

The insulator 550 functions as a first gate insulating film. Like the insulator 524, the insulator 550 is preferably formed using an insulator that contains excess oxygen and releases oxygen by heating.

Specifically, silicon oxide containing excess oxygen, silicon oxynitride, silicon nitride oxide, silicon nitride, silicon oxide to which fluorine is added, silicon oxide to which carbon is added, silicon oxide to which carbon and nitrogen are added, or porous silicon oxide can be used. In particular, silicon oxide and silicon oxynitride are preferable because they are thermally stable.

Furthermore, to efficiently supply excess oxygen contained in the insulator 550 to the oxide 530, a metal oxide may be provided between the insulator 550 and the conductor 560. The metal oxide preferably inhibits diffusion of oxygen from the insulator 550 to the conductor 560. Providing the metal oxide that inhibits diffusion of oxygen inhibits diffusion of excess oxygen from the insulator 550 to the conductor 560. That is, a reduction in the amount of excess oxygen supplied to the oxide 530 can be inhibited. Moreover, oxidation of the conductor 560 due to excess oxygen can be inhibited. As the metal oxide, a material that can be used as the insulator 544 is used.

Note that the insulator 550 may have a stacked-layer structure like the second gate insulating film. As miniaturization and high integration of transistors progress, a problem such as leakage current might arise because of a thinner gate insulating film. For that reason, when the insulator functioning as the gate insulating film has a stacked-layer structure of a high-k material and a thermally stable material, a gate potential during transistor operation can be reduced while the physical thickness is maintained. Furthermore, the stacked-layer structure can be thermally stable and have a high dielectric constant.

Although the conductor 560 that functions as the first gate electrode and has a two-layer structure is shown in FIG. 14A and FIG. 14B, a single-layer structure or a stacked-layer structure of three or more layers may be employed.

As the conductor 560a, it is preferable to use a conductive material having a function of inhibiting diffusion of impurities such as a hydrogen atom, a hydrogen molecule, a water molecule, a nitrogen atom, a nitrogen molecule, a nitrogen oxide molecule ($N_2O$, NO, $NO_2$, and the like), and a copper atom. Alternatively, it is preferable to use a conductive material having a function of inhibiting diffusion of oxygen (e.g., at least one of an oxygen atom and an oxygen molecule). When the conductor 560a has a function of inhibiting diffusion of oxygen, it is possible to inhibit a reduction in conductivity of the conductor 560b due to oxidation caused by oxygen contained in the insulator 550. As a conductive material having a function of inhibiting diffusion of oxygen, for example, tantalum, tantalum nitride, ruthenium, ruthenium oxide, or the like is preferably used. For the conductor 560a, the oxide semiconductor that can be used as the oxide 530 can be used. In that case, when the conductor 560b is deposited by a sputtering method, the conductor 560a can have a reduced electrical resistance value to be a conductor. Such a conductor can be referred to as an OC (Oxide Conductor) electrode.

In addition, a conductive material containing tungsten, copper, or aluminum as its main component is preferably used for the conductor 560b. Furthermore, the conductor 560b also functions as a wiring and thus a conductor having high conductivity is preferably used as the conductor 560b. For example, a conductive material containing tungsten, copper, or aluminum as its main component can be used. Moreover, the conductor 560b may have a stacked-layer structure, for example, a stacked-layer structure of the above conductive material and titanium or titanium nitride.

The insulator 580 is provided over the conductor 542*a* and the conductor 542*b* with the insulator 544 therebetween. The insulator 580 preferably includes an excess-oxygen region. For example, the insulator 580 preferably contains silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, resin, or the like. In particular, silicon oxide and silicon oxynitride are preferable because they are thermally stable. In particular, silicon oxide and porous silicon oxide are preferable because an excess-oxygen region can be easily formed in a later step.

The insulator 580 preferably includes an excess-oxygen region. When the insulator 580 that releases oxygen by heating is provided in contact with the insulator 550, oxygen in the insulator 580 can be efficiently supplied to the oxide 530 through the insulator 550. Note that the concentration of impurities such as water or hydrogen in the insulator 580 is preferably reduced.

The opening of the insulator 580 is formed to overlap with the region between the conductor 542*a* and the conductor 542*b*. Accordingly, the conductor 560 is formed to be embedded in the opening of the insulator 580 and the region between the conductor 542*a* and the conductor 542*b*.

The gate length needs to be short for miniaturization of the semiconductor device, but it is necessary to prevent a reduction in conductivity of the conductor 560. When the conductor 560 is made thick to achieve this, the conductor 560 might have a shape with a high aspect ratio. In this embodiment, the conductor 560 is provided to be embedded in the opening of the insulator 580; thus, even when the conductor 560 has a shape with a high aspect ratio, the conductor 560 can be formed without collapsing during the process.

The insulator 574 is preferably provided in contact with a top surface of the insulator 580, a top surface of the conductor 560, and a top surface of the insulator 550. When the insulator 574 is deposited by a sputtering method, excess-oxygen regions can be provided in the insulator 550 and the insulator 580. Accordingly, oxygen can be supplied from the excess-oxygen regions to the oxide 530.

For example, a metal oxide containing one kind or two or more kinds selected from hafnium, aluminum, gallium, yttrium, zirconium, tungsten, titanium, tantalum, nickel, germanium, magnesium, and the like can be used as the insulator 574.

In particular, aluminum oxide has a high barrier property, and even a thin aluminum oxide film having a thickness of greater than or equal to 0.5 nm and less than or equal to 3.0 nm can inhibit diffusion of hydrogen and nitrogen. Accordingly, aluminum oxide deposited by a sputtering method serves as an oxygen supply source and can also have a function of a barrier film against impurities such as hydrogen.

In addition, an insulator 581 functioning as an interlayer film is preferably provided over the insulator 574. As in the insulator 524 or the like, the concentration of impurities such as water or hydrogen in the insulator 581 is preferably reduced.

Furthermore, a conductor 540*a* and a conductor 540*b* are positioned in openings formed in the insulator 581, the insulator 574, the insulator 580, and the insulator 544. The conductor 540*a* and the conductor 540*b* are provided to face each other with the conductor 560 therebetween. The structures of the conductor 540*a* and the conductor 540*b* are similar to a structure of a conductor 546 and a conductor 548 that are described later. Furthermore, as illustrated in FIG. 14A, an insulator having a function of a barrier film against impurities such as hydrogen may be provided between the sidewall of the opening and the conductor 540*a* or the conductor 540*b*.

An insulator 582 is provided over the insulator 581. A substance having a barrier property against oxygen or hydrogen is preferably used for the insulator 582. Therefore, a material similar to that for the insulator 514 can be used for the insulator 582. For the insulator 582, a metal oxide such as aluminum oxide, hafnium oxide, or tantalum oxide is preferably used, for example.

In particular, aluminum oxide has an excellent blocking effect that prevents the passage of both oxygen and impurities such as hydrogen and moisture which are factors of a change in electrical characteristics of the transistor. Accordingly, aluminum oxide can prevent mixing of impurities such as hydrogen and moisture into the transistor 500 in a manufacturing process and after manufacturing of the transistor. In addition, release of oxygen from the oxide included in the transistor 500 can be inhibited. Therefore, aluminum oxide is suitably used for a protective film of the transistor 500.

In addition, an insulator 586 is provided over the insulator 582. For the insulator 586, a material similar to that for the insulator 320 can be used. Furthermore, when a material with a comparatively low dielectric constant is used for these insulators, parasitic capacitance generated between wirings can be reduced. A silicon oxide film, a silicon oxynitride film, or the like can be used for the insulator 586, for example.

Furthermore, the conductor 546, the conductor 548, and the like are embedded in the insulator 522, the insulator 524, the insulator 544, the insulator 580, the insulator 574, the insulator 581, the insulator 582, and the insulator 586.

The conductor 546 and the conductor 548 have functions of plugs or wirings that are connected to the capacitor 800, the transistor 500, or the transistor 300. The conductor 546 and the conductor 548 can be provided using materials similar to those for the conductor 328 and the conductor 330.

Next, the capacitor 800 is provided above the transistor 500. The capacitor 800 includes a conductor 810, a conductor 820, and an insulator 830.

In addition, a conductor 812 may be provided over the conductor 546 and the conductor 548. The conductor 812 has a function of a plug or a wiring that is connected to the transistor 500. The conductor 810 has a function of an electrode of the capacitor 800. The conductor 812 and the conductor 810 can be formed at the same time.

For the conductor 812 and the conductor 810, a metal film containing an element selected from molybdenum, titanium, tantalum, tungsten, aluminum, copper, chromium, neodymium, and scandium; a metal nitride film containing any of the above elements as its component (a tantalum nitride film, a titanium nitride film, a molybdenum nitride film, or a tungsten nitride film); or the like can be used. Alternatively, it is possible to use a conductive material such as indium tin oxide, indium oxide containing tungsten oxide, indium zinc oxide containing tungsten oxide, indium oxide containing titanium oxide, indium tin oxide containing titanium oxide, indium zinc oxide, or indium tin oxide to which silicon oxide is added.

Although the conductor 812 and the conductor 810 each having a single-layer structure are shown in FIG. 12, the structure is not limited thereto; a stacked-layer structure of two or more layers may be employed. For example, between a conductor having a barrier property and a conductor having high conductivity, a conductor that is highly adhesive to the conductor having a barrier property and the conductor having high conductivity may be formed.

The conductor 820 is provided so as to overlap with the conductor 810 with the insulator 830 positioned therebetween. The conductor 820 can be formed using a conductive material such as a metal material, an alloy material, or a metal oxide material. It is preferable to use a high-melting-point material that has both heat resistance and conductivity, such as tungsten or molybdenum, and it is particularly preferable to use tungsten. In addition, in the case where the conductor is formed concurrently with another component such as a conductor, Cu (copper), Al (aluminum), or the like, which is a low-resistance metal material, is used.

An insulator 840 is provided over the conductor 820 and the insulator 830. The insulator 840 can be provided using a material similar to that for the insulator 320. The insulator 840 may function as a planarization film that covers an uneven shape thereunder.

With the use of this structure, a change in electrical characteristics can be inhibited and reliability can be improved in a semiconductor device using a transistor including an oxide semiconductor. Alternatively, a memory device, an arithmetic device, or the like using a transistor including an oxide semiconductor can be miniaturized or highly integrated.

[Metal Oxide]

A metal oxide that can be used for the semiconductor layer (the oxide 530) where the channel of the transistor is formed is described below.

Note that in this specification and the like, a metal oxide containing nitrogen is also collectively referred to as a metal oxide in some cases. A metal oxide containing nitrogen may be referred to as a metal oxynitride. For example, a metal oxide containing nitrogen, such as zinc oxynitride (ZnON), may be used for the semiconductor layer.

Note that in this specification and the like, "CAAC (c-axis aligned crystal)" or "CAC (Cloud-Aligned Composite)" might be stated. Note that CAAC refers to an example of a crystal structure, and CAC refers to an example of a function or a material composition.

For example, a CAC (Cloud-Aligned Composite)-OS (Oxide Semiconductor) can be used for the semiconductor layer.

A CAC-OS or a CAC-metal oxide has a conducting function in part of the material and has an insulating function in another part of the material; as a whole, the CAC-OS or the CAC-metal oxide has a function of a semiconductor. Note that in the case where the CAC-OS or the CAC-metal oxide is used in an active layer of a transistor, the conducting function is a function that allows electrons (or holes) serving as carriers to flow, and the insulating function is a function that does not allow electrons serving as carriers to flow. By the complementary action of the conducting function and the insulating function, a switching function (On/Off function) can be given to the CAC-OS or the CAC-metal oxide. In the CAC-OS or the CAC-metal oxide, separation of the functions can maximize each function.

Furthermore, the CAC-OS or the CAC-metal oxide includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

Furthermore, in the CAC-OS or the CAC-metal oxide, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

Furthermore, the CAC-OS or the CAC-metal oxide includes components having different bandgaps. For example, the CAC-OS or the CAC-metal oxide includes a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS or CAC-metal oxide is used in a channel formation region of a transistor, high current driving capability in an on state of the transistor, that is, a high on-state current and high field-effect mobility can be obtained.

In other words, the CAC-OS or the CAC-metal oxide can also be referred to as a matrix composite or a metal matrix composite.

Oxide semiconductors (metal oxides) can be classified into a single crystal oxide semiconductor and a non-single-crystal oxide semiconductor. Examples of a non-single-crystal oxide semiconductor include a CAAC-OS (c-axis aligned crystalline oxide semiconductor), a polycrystalline oxide semiconductor, an nc-OS (nanocrystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

Furthermore, the CAAC-OS tends to have a layered crystal structure (also referred to as a layered structure) in which a layer containing indium and oxygen (hereinafter, In layer) and a layer containing the element M, zinc, and oxygen (hereinafter, (M,Zn) layer) are stacked. Note that indium and the element M can be replaced with each other, and when the element M in the (M,Zn) layer is replaced with indium, the layer can also be referred to as an (In,M,Zn)

layer. Furthermore, when indium in the In layer is replaced with the element M, the layer can be referred to as an (In,M) layer.

The CAAC-OS is a metal oxide with high crystallinity. On the other hand, a clear crystal grain boundary cannot be observed in the CAAC-OS; thus, it can be said that a reduction in electron mobility due to the crystal grain boundary is less likely to occur. Entry of impurities, formation of defects, or the like might decrease the crystallinity of a metal oxide; thus, it can be said that the CAAC-OS is a metal oxide that has small amounts of impurities and defects (e.g., oxygen vacancies (also referred to as $V_O$)). Thus, a metal oxide including a CAAC-OS is physically stable. Therefore, the metal oxide including a CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter referred to as IGZO) that is a kind of metal oxide containing indium, gallium, and zinc has a stable structure in some cases by being formed of the above-described nanocrystals. In particular, crystals of IGZO tend not to grow in the air and thus, a stable structure is obtained when IGZO is formed of smaller crystals (e.g., the above-described nanocrystals) rather than larger crystals (here, crystals with a size of several millimeters or several centimeters).

An a-like OS is a metal oxide having a structure between those of the nc-OS and an amorphous oxide semiconductor. The a-like OS includes a void or a low-density region. That is, the a-like OS has low crystallinity as compared with the nc-OS and the CAAC-OS.

An oxide semiconductor (metal oxide) can have various structures which show different properties. Two or more of the amorphous oxide semiconductor, the polycrystalline oxide semiconductor, the a-like OS, the nc-OS, and the CAAC-OS may be included in an oxide semiconductor of one embodiment of the present invention.

A metal oxide film that functions as a semiconductor layer can be formed using either or both of an inert gas and an oxygen gas. Note that there is no particular limitation on the flow rate ratio of oxygen (the partial pressure of oxygen) at the time of forming the metal oxide film. However, to obtain a transistor having high field-effect mobility, the flow rate ratio of oxygen (the partial pressure of oxygen) at the time of forming the metal oxide film is preferably higher than or equal to 0% and lower than or equal to 30%, further preferably higher than or equal to 5% and lower than or equal to 30%, still further preferably higher than or equal to 7% and lower than or equal to 15%.

The energy gap of the metal oxide is preferably 2 eV or more, further preferably 2.5 eV or more, still further preferably 3 eV or more. With the use of a metal oxide having such a wide energy gap, the off-state current of the transistor can be reduced.

The substrate temperature during the formation of the metal oxide film is preferably lower than or equal to 350° C., further preferably higher than or equal to room temperature and lower than or equal to 200° C., still further preferably higher than or equal to room temperature and lower than or equal to 130° C. The substrate temperature at the time of depositing the metal oxide film is preferably room temperature because productivity can be increased.

The metal oxide film can be formed by a sputtering method. Alternatively, for example, a PLD method, a PECVD method, a thermal CVD method, an ALD method, or a vacuum evaporation method may be used.

At least part of this embodiment can be implemented in combination with the other embodiments described in this specification as appropriate.

REFERENCE NUMERALS

R1, R2, G1, G2, B1, B2: display element, S0, S1, S2: image signal, 10, 10a: composite device, 11: display device, 12, 12a: sensor device, 13: information processing device, 21: control portion, 22: display portion, 23: image capturing portion, 24: lens, 25: communication portion, 25a: returning operation, 25b: processing operation, 25c: resting operation, 26: image generation portion, 27: signal, 31: sensor portion, 32: communication portion, 33: signal, 33a: pulse signal, 33b: signal, 34: display portion, 40: user, 41: eyeball, 42: arm, 43: finger, 44: upper arm, 45: clothes, 50a, 50b, 50c: image, 51a, 51b, 51c: image information This application is based on Japanese Patent Application Serial No. 2019-107172 filed on Jun. 7, 2019, the entire contents of which are hereby incorporated herein by reference.

The invention claimed is:

1. A composite device comprising:
   a sensor device including a first communication portion and a sensor portion; and
   a display device including a display portion, a second communication portion, an image generation portion, and an image capturing portion,
   wherein the sensor portion is capable of being worn on a human body,
   wherein the first communication portion is configured to transmit a pulse signal and a signal including information obtained by the sensor portion,
   wherein the second communication portion is configured to receive the signal,
   wherein the image generation portion is configured to generate first image data on the basis of the information and second image data supplied from the image capturing portion,
   wherein the image generation portion is configured to output the first image data to the display portion, and
   wherein the display portion is configured to display an image on the basis of the first image data so that a first image showing the information is superimposed on a second image taken by the image capturing portion.

2. The composite device according to claim 1, wherein the sensor device is capable of being worn on an eyeball.

3. The composite device according to claim 1, wherein the sensor device is capable of being attached to skin.

4. The composite device according to claim 1, wherein the sensor device is capable of being worn on a wrist, a finger, or an arm.

5. The composite device according to claim 1, wherein the sensor portion is configured to detect one or more of a blood sugar level, a heart rate, a blood pressure, a body temperature, a degree of oxygen saturation, and a neutral fat concentration.

6. The composite device according to claim 1, further comprising a control portion, wherein the control portion is configured to return from a resting state in accordance with the signal.

7. The composite device according to claim 1, further comprising a control portion,
wherein the control portion has a semiconductor device, and
wherein the semiconductor device is configured to perform power gating.

8. A composite device comprising:
a sensor device including a first communication portion and a sensor portion; and
a display device including a display portion, a second communication portion, and an image generation portion,
wherein the sensor portion is capable of being worn on a human body,
wherein the first communication portion is configured to transmit a pulse signal and a signal including information obtained by the sensor portion,
wherein the second communication portion is configured to receive the signal,
wherein the image generation portion is configured to generate first image data on the basis of the information,
wherein the image generation portion is configured to output the first image data to the display portion, and
wherein the display portion is configured to display an image on the basis of the first image data so that a first image showing the information is superimposed on a second image.

9. The composite device according to claim 8, wherein the sensor device is capable of being worn on an eyeball.

10. The composite device according to claim 8, wherein the sensor device is capable of being attached to skin.

11. The composite device according to claim 8, wherein the sensor device is capable of being worn on a wrist, a finger, or an arm.

12. The composite device according to claim 8, wherein the sensor portion is configured to detect one or more of a blood sugar level, a heart rate, a blood pressure, a body temperature, a degree of oxygen saturation, and a neutral fat concentration.

13. The composite device according to claim 8, further comprising a control portion,
wherein the control portion is configured to return from a resting state in accordance with the signal.

14. The composite device according to claim 8, further comprising a control portion,
wherein the control portion has a semiconductor device, and
wherein the semiconductor device is configured to perform power gating.

* * * * *